(12) United States Patent (10) Patent No.: US 7,853,311 B1
Webb (45) Date of Patent: Dec. 14, 2010

(54) SURGICAL TARGETING SYSTEM

(75) Inventor: Lawrence Xavier Webb, Winston-Salem, NC (US)

(73) Assignee: 3M Innovative Properties Company, St. Paul, MN (US)

( * ) Notice: Subject to any disclaimer, the term of this patent is extended or adjusted under 35 U.S.C. 154(b) by 1707 days.

(21) Appl. No.: 09/553,683

(22) Filed: Apr. 21, 2000

Related U.S. Application Data

(60) Provisional application No. 60/130,920, filed on Apr. 23, 1999.

(51) Int. Cl.
*A61B 5/00* (2006.01)
(52) U.S. Cl. ...................................... 600/426; 128/849
(58) Field of Classification Search ................ 600/425, 600/426, 429, 407; 378/164, 20, 205, 163; 128/849, 852, 853; 606/130
See application file for complete search history.

(56) References Cited

U.S. PATENT DOCUMENTS

| | | | | |
|---|---|---|---|---|
| 2,344,824 A | | 3/1944 | Landis et al. ................. | 250/65 |
| 3,171,959 A | | 3/1965 | Kozek et al. .................. | 250/53 |
| 3,547,121 A | * | 12/1970 | Cherry ........................ | 128/215 |
| 3,968,792 A | | 7/1976 | Small .......................... | 128/132 |
| 4,181,859 A | | 1/1980 | Vitalini ....................... | 250/476 |
| 4,187,423 A | | 2/1980 | Ehrhardt ..................... | 250/312 |
| 4,319,136 A | * | 3/1982 | Jinkins ........................ | 250/456 |
| 4,349,498 A | | 9/1982 | Ellis et al. .................... | 264/81 |
| 4,506,676 A | | 3/1985 | Duska ........................ | 128/653 |

(Continued)

FOREIGN PATENT DOCUMENTS

EP 0 387 103 A1 9/1990

(Continued)

OTHER PUBLICATIONS

International Preliminary Examining Authority, PCT International Preliminary Examination Report and Notification of Transmittal thereof for International Application No. PCT/US01/12691, Sep. 17, 2002, 4 pages.

(Continued)

*Primary Examiner*—Brian Casler
*Assistant Examiner*—Jonathan G Cwern

(57) ABSTRACT

A targeting device for providing a series of coordinates/lines within a sheet of sterile, flexible material with an adherent surface which is applied to the skin (after suitable surgical preparation). The sheet is non-porous and may have a topical antiseptic on the side which is applied to the skin. A fluoroscope or roentgenographic image of the portion of the body to which the adherent film is applied will show the underlying skeletal and radiopaque elements as well as the overlying surgical grid. Once the targeting device is applied, the coordinates on the grid lines are clearly visible on the surface of the skin as well as on the fluoroscopic or radiographic image and by knowing the direction of the fluoroscopic or radiographic beam, the operator will be able to thereby correlate a specific locus on the skin with an underlying skeletal element or other underlying radiopaque structure. By applying the targeting device to the part of the body in a circumferential or nearly circumferential manner, and utilizing a radiolucent operating room table, and a radiograph or C-arm fluoroscope, targeting techniques using the targeting device can be utilized at surgery. Multiple targeting or percutaneous procedures can be performed at the same sitting with the application of a single device.

31 Claims, 19 Drawing Sheets

U.S. PATENT DOCUMENTS

| | | | |
|---|---|---|---|
| 4,627,427 A | 12/1986 | Arco | |
| 4,813,062 A | 3/1989 | Gilpatrick | 378/162 |
| 4,838,265 A * | 6/1989 | Cosman et al. | 128/303 |
| 4,860,331 A | 8/1989 | Williams et al. | 378/163 |
| 4,899,762 A * | 2/1990 | Muller | 128/850 |
| 4,916,170 A | 4/1990 | Nambu et al. | 523/137 |
| 4,918,715 A | 4/1990 | Krupnick et al. | 378/164 |
| 4,938,233 A * | 7/1990 | Orrison, Jr. | 128/849 |
| 4,985,019 A | 1/1991 | Michelson | 604/180 |
| 5,052,035 A | 9/1991 | Krupnick | 378/163 |
| 5,068,886 A | 11/1991 | Lavia | 378/164 |
| 5,105,457 A | 4/1992 | Glassman | 378/163 |
| 5,216,700 A | 6/1993 | Cherian | 378/163 |
| 5,239,569 A | 8/1993 | Saleh et al. | 378/163 |
| 5,242,985 A * | 9/1993 | Shih et al. | 525/326.9 |
| 5,260,985 A * | 11/1993 | Mosby | 378/164 |
| 5,285,785 A | 2/1994 | Meyer | 128/653.1 |
| 5,306,271 A | 4/1994 | Zinreich et al. | 606/1 |
| 5,383,234 A | 1/1995 | Russell | 378/164 |
| 5,394,456 A | 2/1995 | Livingston | 378/162 |
| 5,419,324 A | 5/1995 | Dillow | 128/653.1 |
| 5,427,099 A | 6/1995 | Adams | 128/653.1 |
| 5,444,754 A | 8/1995 | Wederhorn et al. | 378/38 |
| 5,476,016 A | 12/1995 | Fedorka-Cray et al. | 73/863 |
| 5,522,921 A | 6/1996 | Custer | 106/21 R |
| 5,582,189 A | 12/1996 | Pannozzo | |
| 5,682,890 A * | 11/1997 | Kormos et al. | 600/417 |
| 5,692,519 A | 12/1997 | Luderer et al. | 128/754 |
| 5,702,128 A | 12/1997 | Maxim et al. | 283/81 |
| 5,743,899 A | 4/1998 | Zinreich | 606/1 |
| 5,799,059 A | 8/1998 | Stembridge et al. | 378/207 |
| 5,891,034 A | 4/1999 | Bucholz | 600/426 |
| 5,908,387 A | 6/1999 | LeFree et al. | 600/425 |
| 6,013,035 A | 1/2000 | Unger et al. | 600/562 |
| 6,041,064 A | 3/2000 | Kurdzo et al. | 370/466 |
| 6,041,094 A | 3/2000 | Russell | 378/37 |
| 6,173,201 B1 * | 1/2001 | Front | 600/429 |
| 6,301,495 B1 * | 10/2001 | Gueziec et al. | 600/407 |
| 6,333,970 B1 | 12/2001 | LeMaitre et al. | 378/162 |
| 6,356,621 B1 | 3/2002 | Furumori et al. | |
| 6,419,680 B1 * | 7/2002 | Cosman et al. | 606/130 |

FOREIGN PATENT DOCUMENTS

| | | | |
|---|---|---|---|
| EP | 03-871-03 | * | 12/1990 |
| GB | 2 292 890 A | | 3/1996 |
| WO | WO 00/54713 A1 | | 9/2000 |
| WO | WO 01/80738 A1 | | 11/2001 |

OTHER PUBLICATIONS

Alexander et al., "Development of a Safe and Effective One-Minute Preoperative Skin Preparation," Arch Surg, vol. 120, pp. 1357-1361 (Dec. 1985).

Dewan et al., "The Use of an Iodophor-Impregnated Plastic Incise Drape in Abdominal Surgery—A Controlled Clinical Trial," Aust., N.Z. Journal of Surgery, vol. 57, Title page, Publication page, Table of Contents, and pp. 859-863 (8 pgs total)(1987).

French et al., "The Plastic Surgical Adhesive Drape: An Evaluation of Its Efficacy as a Microbial Barrier," Annals of Surgery, vol. 184, No. 1, Title page, Publication page, Table of Contents, and pp. 46-50 (10 pgs total)(Jul. 1976).

Johnston et al., "Rate of Bacterial Recolonization of the Skin After Preparation: Four Methods Compared," British Journal of Surgery, vol. 74, p. 64 (Jan. 1987).

Levy et al., "Contamination Reduction During Central Venous Catheterization," Critical Care Medicine, vol. 16, No. 2, Title page, Publication page, Table of Contents, and pp. 165-167 (6 pgs total)(Feb. 1988).

Ritter et al., "Retrospective Evaluation of an Iodophor-Incorporated Antimicrobial Plastic Adhesive Wound Drape," Clinical Orthopaedics and Related Research, No. 228, Title page, Publication page, Table of Contents, and pp. 307-308 (8 pgs total) (Mar. 1988).

PCT International Search Report, and PCT Notification thereof for International Application No. PCT/US01/12691, mailed Sep. 26, 2001, Form PCT/ISA/210 (first and second sheets) (Jul. 1998), Form PCT/ISA/220 (Jul. 1998).

* cited by examiner

Figure 3

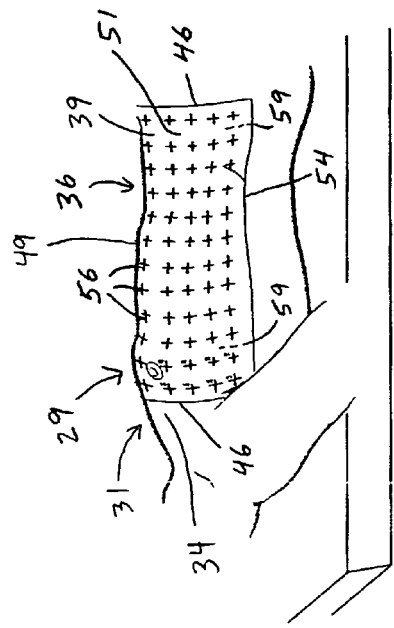
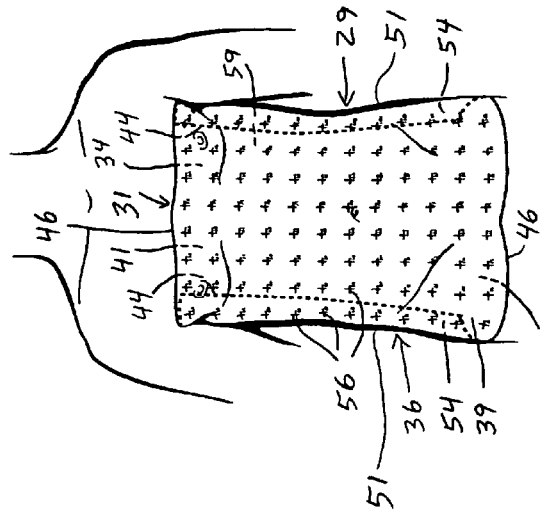
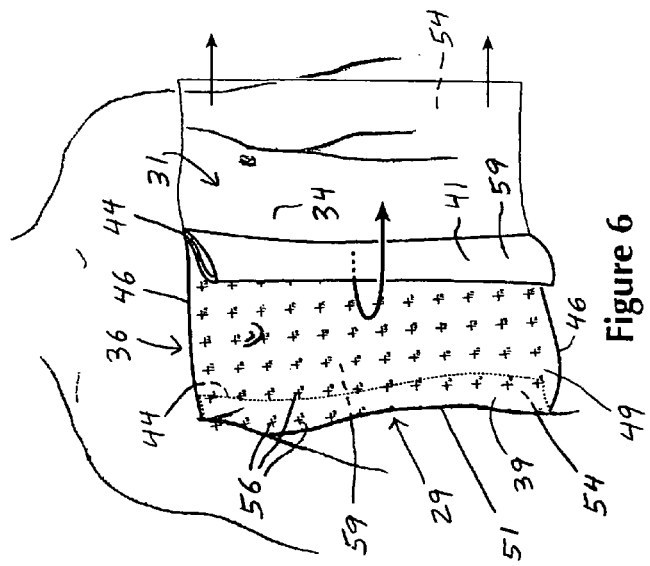

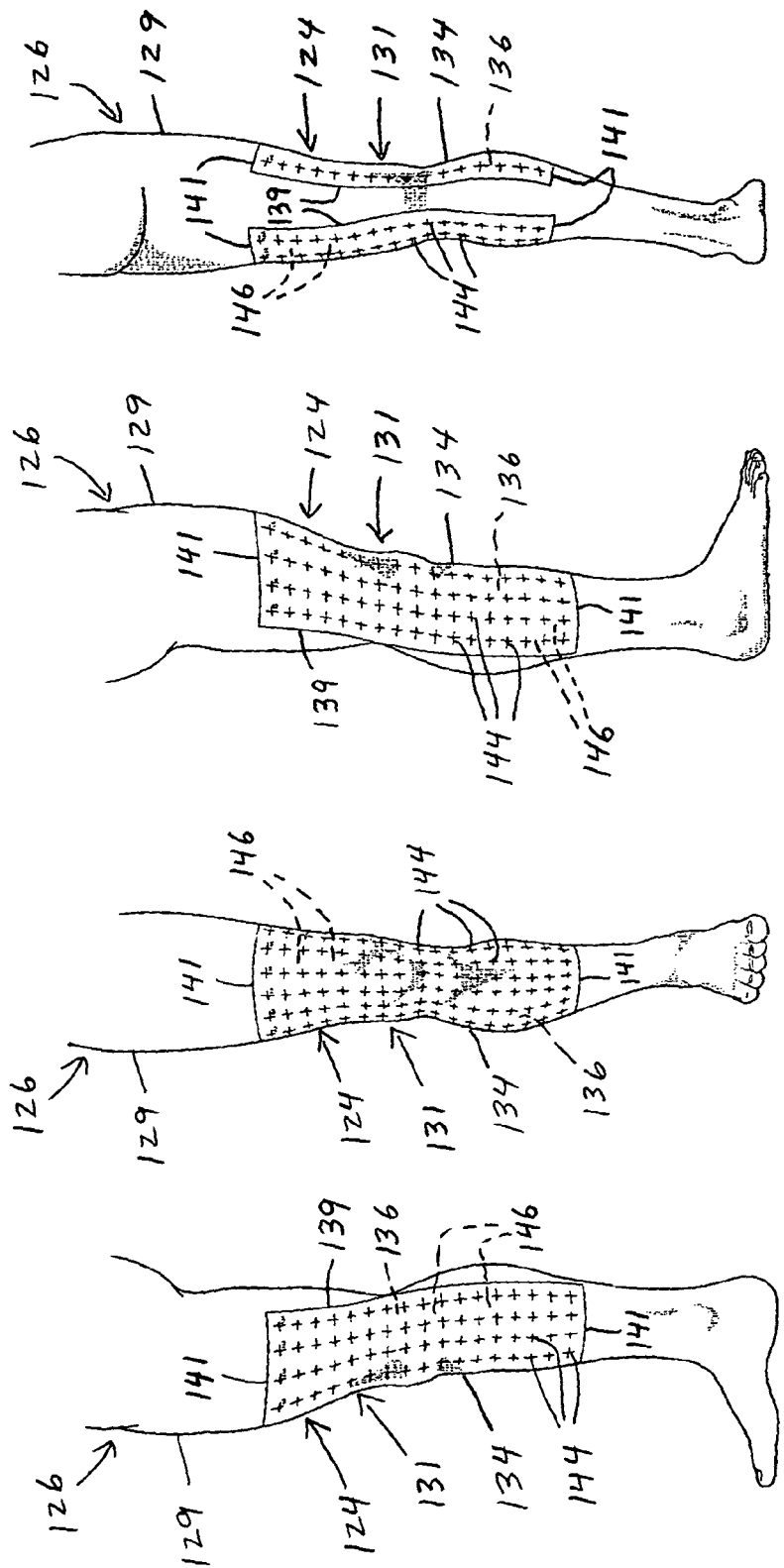

SURGICAL TARGETING SYSTEM

This application claims the benefit of U.S. Provisional Application No. 60/130,920, filed Apr. 23, 1999, the entire disclosure of which is hereby incorporated by reference herein.

BRIEF STATEMENT OF THE INVENTION

The surgical targeting system of the present invention is a device that allows the surgeon to intraoperatively pinpoint a location as well as the surgical corridor for accessing that location within the confines of the human body using fluoroscopy or other radiographic imaging modalities while maintaining and safeguarding a sterile surgical field. If there is a visible laser light beam (parallel to the beam of the X-ray) on the emitter and receiver tube of the C-arm fluoroscope, the device also enables the operator to obtain projections or fluoroscopic views or X-rays identical to one gotten earlier in a procedure during which multiple other intervening views have been taken.

Once a desired target site has been found on the fluoroscopy monitor, it may be transferred directly to the corresponding exterior location on the patient. The point of skin incision as well as the angle of incidence of the surgical corridor (for instrument or implant placement) are given by the locus on the grid and the direction of the radiographic/fluoroscopic beam (which can be altered in three dimensions). By applying the device to the skin of the patient's body and/or body part e.g., limb circumferentially or hemicircumferentially, the operator may take advantage of a parallax effect for more precise targeting and the corridor can be "visualized" or determined by the surgeon in three dimensions. Thus, for example, by utilizing two systems placed on two body surfaces situated on opposite surfaces of the body/body part, a specific locus which simultaneously resides between the imaged surgical targeting systems can be percutaneously accessed via the collinear corridor given by the direction of the fluoroscopic X-ray beam, and the near and far surgical targeting system grid coordinates. The depth of advancement of the surgical instrument or implant is given by a fluoroscopic/X-ray view (with overlying surgical targeting grid) taken at right angles to the first.

Also, if the depth of the target and the ratio of its distance from the skin of the "near" grid to the "far" grid determined (by an X-ray or fluoroscopic view) then comparison of near and far grids with an intervening target tissue or implant or foreign body and notation of corresponding collinear near and far grid coordinates can be used to mathematically derive other collinear near grid coordinate—target far grid coordinate combinations—without the need for a series of further "empiric" or trial fluoroscopic or X-ray views.

BACKGROUND OF THE INVENTION

It is common practice in the taking of medical X-rays to place a pre-shaped lead marker on a portion of the patient's body to be examined. In common practice, for example, the lead marker "R" or "L" are used to distinguish the right from the left side of the body. Other markers serve to provide a visual reference point in the resultant X-ray film to facilitate interpretation of the X-ray. Once the preferred body structure has been determined on the film, its location can be ascertained relative to this lead marker.

It is also common practice in surgery (for cases in which fluoroscopic X-rays are utilized as a means of guiding the placement of instruments or implants during the procedure) to use a sterile surgical instrument by means holding it over a specific point on the patient's skin (after it has been prepped as a sterile field) while obtaining a fluoroscopic image. This enables the surgeon to plan the skin entry point of a percutaneous procedure. By acquiring the image with the tip of a superimposed surgical instrument held at the same locus on the patient's skin, an assessment of position relative to structures seen on the fluoroscopic image can be ascertained by the surgeon. If the first position selected by the surgeon is off the desired point on the fluoroscopic image, an adjustment is made by moving the instrument to a new locus and a second image is obtained. This procedure is repeated until the overlying instrument is at the correct spot on the skin corresponding to the appropriate locus on the fluoroscopic image. By moving the C-arm fluoroscope so that the direction of the beam is at 90 degrees to the initial one, an assessment of depth to the target locus can be made. This is the process that is utilized when finding the correct start point on the outer distal femur for interlocking nailing (with the modification of depth assessment where the second view is often obtained to verify screw length) and applies to circumstances where the instrument or implant is to be advanced "end on" the target tissue and parallel to the direction of the fluoroscopic or roentgenographic beam. In instances where this is not the case, e.g., when the start point for an intramedullary nailing on the skin needs to be determined, knowing that this position on the skin must be collinear with the proximal femoral shaft, the assessment of colinearity can be accomplished by applying the surgical targeting grid of the present invention so that it is collinear with the proximal femur on the lateral aspect (this may require C-arm fluoroscopic X-ray check during the act of grid placement, with extension of the placement cephalad as far as the buttock) as well placement of a second grid on the anterior aspect with extension cephalad as far as the buttock at which point it overlaps the first surgical targeting system. By noting which grid row overlies the proximal femoral canal on the anteroposterior projection and also noting which grid row from the second surgical targeting system overlies the proximal femoral canal on the lateral projection, the start point on the skin is given by the intersection of these two rows on the surface of the buttock area. This is of special importance in percutaneous intramedullary nailing procedures, where the selection of an incision point which is not collinear with the proximal femur may cause tenting of a large cuff of soft tissue during the procedure and may necessitate extension of a small incision. Finding this point on the skin might otherwise entail multiple fluoroscopic X-ray views, each of which impart radiation exposure to the patient as well as the surgeon and other operating room personnel. An additional point is that accurate location of this point permits a small skin incision and this, with healing becomes a small scar which, if later extraction of the device is opted for, facilitates the accomplishment of the procedure, again, as a percutaneous one (with a limited incision whose locus is given by the existing scar).

Another example of the utility of the system of the present invention provided by the procedure of reamed femoral intramedullary nailing. When the currently commonly utilized process (using an overlying radiopaque object to find a locus on the skin as described above) is used to monitor the passage of a surgical instrument down a surgical corridor, multiple additional fluoroscopic views may be needed. An example of this would be passage of a guidewire down an intramedullary canal for a fracture of the femur. Knowing which direction to point the angled tip of the guide wire entails knowing which direction the fragment on the other side of the fracture is displaced. Additional spot fluoroscopic views of the fracture with an overlying radiopaque object (such as a hemostat clamp, such as for clamping a blood vessel) gives the needed answer and prompts the surgeon to rotate the guidewire so that its tip is toward the intramedullary canal on the displaced fragment before advancing the wire down the fragment's canal. With a surgical targeting device of the present invention in place, obtaining additional fluoroscopic X-rays for this purpose are unnecessary. The added advantageous factor is that the surgeon need not place his hand near the radiation beam with the surgical instrument (this is an occupational hazzard for many surgeons). Additionally, minor directional adjustments in the passage of a radiopaque instrument or implant in the body can be subject to less guesswork because both the coordinates on the fluoroscopic screen and those directly readable on the patient can be correlated. "Guesswork" however may prompt the operator to take more fluoroscopic X-rays or may result in the need for several passes through the patient's tissues with the instrument or implant before the correct corridor is gotten. Having an in place targeting system of the present invention therefore, may provide the surgeon with a series of constant reference points throughout the entirety of the procedure. Having these may facilitate the accuracy and speed of the procedure and diminish the potential hazzard to the patient (additional radiation exposure and damage to tissues from inaccurate passage of instruments or implants under fluoroscopic control) as well as to the surgeon and the operating room personnel (radiation exposure).

U.S. Pat. No. 5,702,128 discloses a radiographic marker system and method of making it. The entire disclosure of U.S. Pat. No. 5,702,128 is hereby incorporated by reference herein. U.S. Pat. No. 5,052,035 (referred to herein as the "'035 patent") discloses image location marking devices for radiographs, a method of marking and methods of use. The entire disclosure of U.S. Pat. No. 5,052,035 is hereby incorporated by reference herein.

Instead of a lead marker, the device disclosed in the '035 patent produces multiple parallel lines on an X-ray film bearing a radiographic image of a patient's body to facilitate the location of a part of the body or a retained foreign body or implant within that image. The device comprises a flexible substrate formed of a porous, translucent or transparent material having lines of a radiopaque material disposed thereon. The device is used by applying it over a selected portion of the patient's body to be X-rayed or scanned using computed tomography (CT). The resulting radiographic image of the selected portion of the person's body thus has indicator lines crossing it, which facilitates the demarcation of a desired portion of that image. A marking instrument, i.e., a marking pen, can be applied to the substrate at predetermined locations thereon while the device is on the person to mark the body at the selected location.

The device disclosed in the '035 patent is non-sterile and, therefore, can only be used in a non-sterile environment. Once the corresponding location has been marked on the patient's body, the device disclosed in the '035 patent is removed and discarded. The biopsy is then carried out normally using the mark placed on the skin as a reference point. If the surgeon would like to take another image with the device disclosed in the '035 patent in place, he would have to compromise the sterile field by replacing the device.

The Ioban® drape is a thin, flexible, adhesive sheet of plastic designed for use during a surgical procedure. The Ioban® drape is 100% impervious to liquid and bacteria, but permeable to oxygen and moisture vapor. Accordingly, a drape that is impervious to liquid strike through or fluid flow through it is an important feature of this device of the present invention. On the other hand, a drape that allows fluid transfer, and thus bacterial transfer, compromises the sterile field. This, in turn, potentially increases the risk of wound infection. For surgical procedures of length, active antimicrobial on the skin in the operative field is a desirable feature. Thus, the inclusion of an antiseptic coating on the drape of the present invention exposed to the skin provides an additional safeguard against infection.

Once a patient's skin has been prepped or prepared for surgery, the sterile Ioban® drape of the present invention is stretched over the area to be incised. The designed function of the Ioban® drape is to provide an added sterile and antiseptic protective barrier within the surgical field placed on the patient's skin and the adjacent operating environment. The Ioban® drape's adhesive properties are often used as a means of securing the sterile drapes or towels to the margins of the surgical field. This feature is an important one when the surgeon is planning a percutaneous procedure with fluoroscopic control, because securing the drapes and towels to the margins of the field in the customary fashion with the use of radiopaque towel clips might otherwise interfere with the ability of the operator to visualize the target or targeted area within the body on the fluoroscopic image.

SUMMARY OF THE INVENTION

This invention consists of a thin radiolucent sheet of translucent or transparent material upon which is located a series of radiographically dense numbered and/or lettered lines or otherwise distinguishable markings. One possibility is to dispose a set of lines at regular intervals and a second set of similarly disposed radiographically dense numbered and/or lettered lines are at right angles to the first, so as to form a series of small distinguishable quadrants or intersecting points, i.e., a grid. Many patterns for the design of these patterns are possible, depending on the particular application. These lines as well as their labels are readily seen directly when applied to the patient's body and are also clearly visible when the area to which they are applied is imaged with fluoroscopic x-rays.

Other features of the invention are that the sheet is sterile and the side that is applied to the patient's skin has a uniform distribution of adhesive (although the amount of adhesive is contingent on the specific application). Additionally, the side of the drape applied to the patient's skin also may have a topical antiseptic. The sheet comes with a second layer on the adhesive side, which readily peels off and allows for application of the adherent portion of the targeting grid sheet to the skin of the patient.

Application of the surgical targeting grid to the surface of the body permits a more accurate localization of radiodense structures or bodies within the zone of targeting by fluoroscopic or radiographic imaging. A surgical instrument or implant can be directed to the target tissue or target object by taking advantage of the surgical targeting system in several ways. For example, once the grid marking or coordinate overlying the target on the fluoroscopic image is located on the surface of the body, that becomes the start point for the passage of the instrument/implant to the target, with care to remain co-linear with the fluoroscopic/X-ray incident beam. Additionally, by disposing the surgical targeting sheet around the portion of the body to be imaged in a hemicircumferential or circumferential manner, two grids (on opposite sides of the body or body part or in different planes from each other e.g., the lateral side and anterior surface of the thorax) can be simultaneously utilized to locate a lesion or a structure. Advantage can thus be taken of the parallax effect of two grids, with one being disposed on the near (to the receiver tube of fluoroscope ((image intensifier)) or developing cassette of the X-ray) body surface and one being disposed on the far or opposite body surface. Determination of depth and relative angle of passage can be ascertained by a grid and corresponding fluoroscopic image or X-ray of the target or passing instrument or implant at right angles to the parallel near and far grids. Overlapping near and far (located on opposite sides of the body or limb) grids can also be utilized in enabling the operator to exactly duplicate a fluoroscopic/X-ray view that was gotten earlier in a procedure. This can occur by making note of overlapping near and far grid coordinates on the view of interest gotten prior. Duplicating this angle of fluoroscopic incident beam can be done by fulfilling this same requirement getting the prior noted grid coordinates to overlap on each other on the image.

Possible methodologies to assure consistent angle of incidence of the fluoroscopic beam can also be facilitated by having a visible laser light beam emanating from an adjustable position on the fluoroscopic emitter tube (X-ray tube) in a direction parallel to the fluoroscopic/X-ray beam. Co-locating the target, the grid marking and the incident visible laser from the emitter tube will allow for more accurate placement of instrument/implant. Once the co-location of the three has occurred (target, grid marking and incident laser light, the operator starts the passage of the instrument/implant at the skin surface at the grid marking which overlies the target on the fluoroscopic view, and maintains the instrument during the course of its passage in line with the incident laser beam. Additional accuracy can be gotten by way of the same technique, but utilizing two surgical targeting grids and having the laser light beam from the receiver tube (also parallel to the fluoroscopic/X-ray beam) centered at the overlapping far grid coordinate on the opposite side of the body/body part.

Other mechanisms for passage of instruments/implants to a target point can be done by utilizing the near and far overlapping grid method, and then utilizing a "C" targeting device.

These and other features and advantages of the invention will be more fully understood from the following description of specific embodiments of the invention taken together with the accompanying drawings.

BRIEF DESCRIPTION OF THE DRAWINGS

FIGS. 3, 4 and 5 are views in the plane of FIG. 1 showing alternative rectangular coordinate configurations of the radiopaque elements of the surgical targeting system;

FIG. 6 is an anterior view of the surgical targeting system of FIG. 1 applied to the torso;

FIG. 7 is a lateral view of the surgical targeting system of FIG. 6 with the patient lying supine on the operating table;

FIG. 8 is an anterior view of the surgical targeting system of FIG. 6 with the patient lying supine on the operating table and viewed from above (anterior aspect);

FIG. 17 is a medial (inner) aspect view of the surgical targeting system of FIG. 1 applied from the mid-thigh to mid-leg levels of a lower limb;

FIG. 18 is an anterior (front) aspect view of the surgical targeting system of FIG. 17 applied from the mid-thigh to mid-leg levels of the lower limb;

FIG. 19 is a lateral (outer) aspect view of the surgical targeting system of FIG. 17 applied from the mid-thigh to mid-leg levels of the lower limb;

FIG. 20 is a posterior (rear) aspect view of the surgical targeting system of FIG. 17 applied from the mid-thigh to mid-leg levels of the lower limb, the surgical targeting system not being applied to the central axial portion of this aspect of the limb;

Corresponding reference characters indicate corresponding parts throughout the several views of the drawings.

DETAILED DESCRIPTION OF THE INVENTION

The surgical targeting system of the present invention combines the advantages of both a marking device for radiograph and a plastic adhesive wound drape such as the Ioban® drape. The device is composed of a thin, sterile flexible, transparent or translucent sheet which has varying amounts of uniformly distributed adhesive and topical/antiseptic such as iodophor on the side which is to be applied to the patient's skin. To facilitate packaging and application to the patient, a removable and disposable layer on the adherent side (which is pealed off when applied) may be incorporated.

Additionally, a series of easily distinguishable radiopaque lines are incorporated either on or within the layers of the drape. One method of distinguishing the radiopaque lines is their being disposed in a pattern and labeled with radiopaque material. The pattern of the radiopaque elements and the labels/coordinates are easily visible on the drape as well as on a radiographic/fluoroscopic image of the drape. The radiopaque medium forms a distinctive pattern of lines on the drape, which allows for easy localization of the pathology or the targeting point within the radiographic image. The radiopaque medium may be, but is not limited to, fine steel wire (having a diameter of 0.003 inches) or a slurry of some radiopaque material such as barium or calcium sulfate.

The material of the lines is radiopaque while the surgical drape material is radiolucent, which means only the lines of the drape and their corresponding coordinate markings are visible when a roentgenographic/fluoroscopic image of the drape is obtained. The drape material is transparent or translucent enough to allow the operator to directly read and distinguish the lines from one another when the drape is applied to the skin of a patient. One method of facilitating this distinction is to make the lines with discrete shapes, such as a zigzag, sine wave, square wave, or loops.

Another method of distinction is straight lines with labels at each intersection that more readily facilitate the identification of the intersection of two of the lines. One possibility is to label the lines numerically along one axis and alphabetically along the other. By doing so, the surgeon is able to visually detect on the fluoroscopy monitor a set of intersecting labeled lines and may thereby distinguish each point of their intersection, such as C4, B2, T9, etc. With this system, each intersection (and each quadrant delineated by four such intersections disposed at the corners of each quadrant) is uniquely identifiable. The proportion of the label to the size of the square is such that it is easily read from the monitor as well as directly and does not interfere with the image within the square. When the squares are small in size, this may necessitate labeling every other row or every few rows or only along the margins of the lines.

Figure 1:
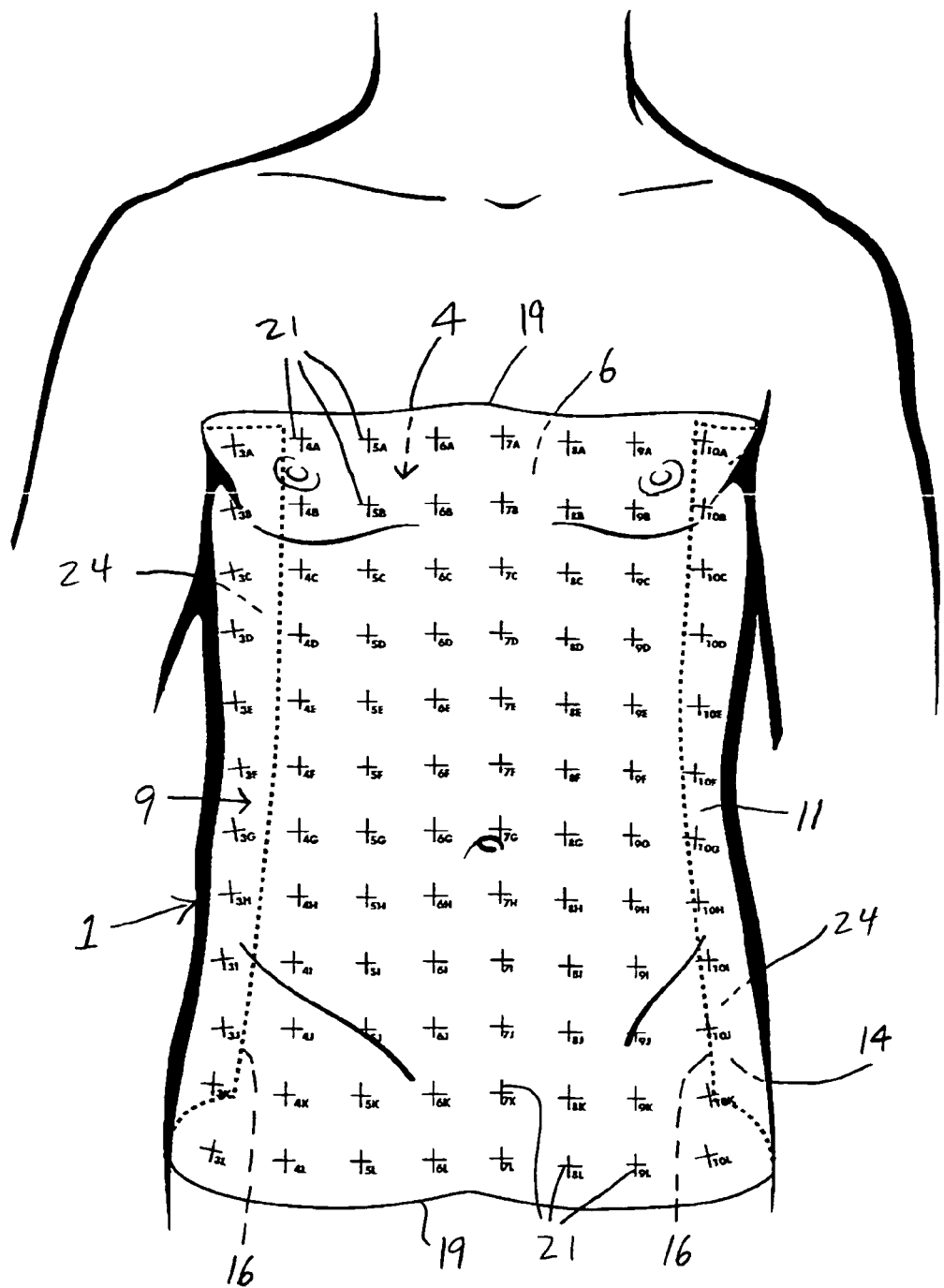
FIG. 1 is an anterior view of an embodiment of the surgical targeting system of the present invention applied to the torso of a body.
Figure 2:
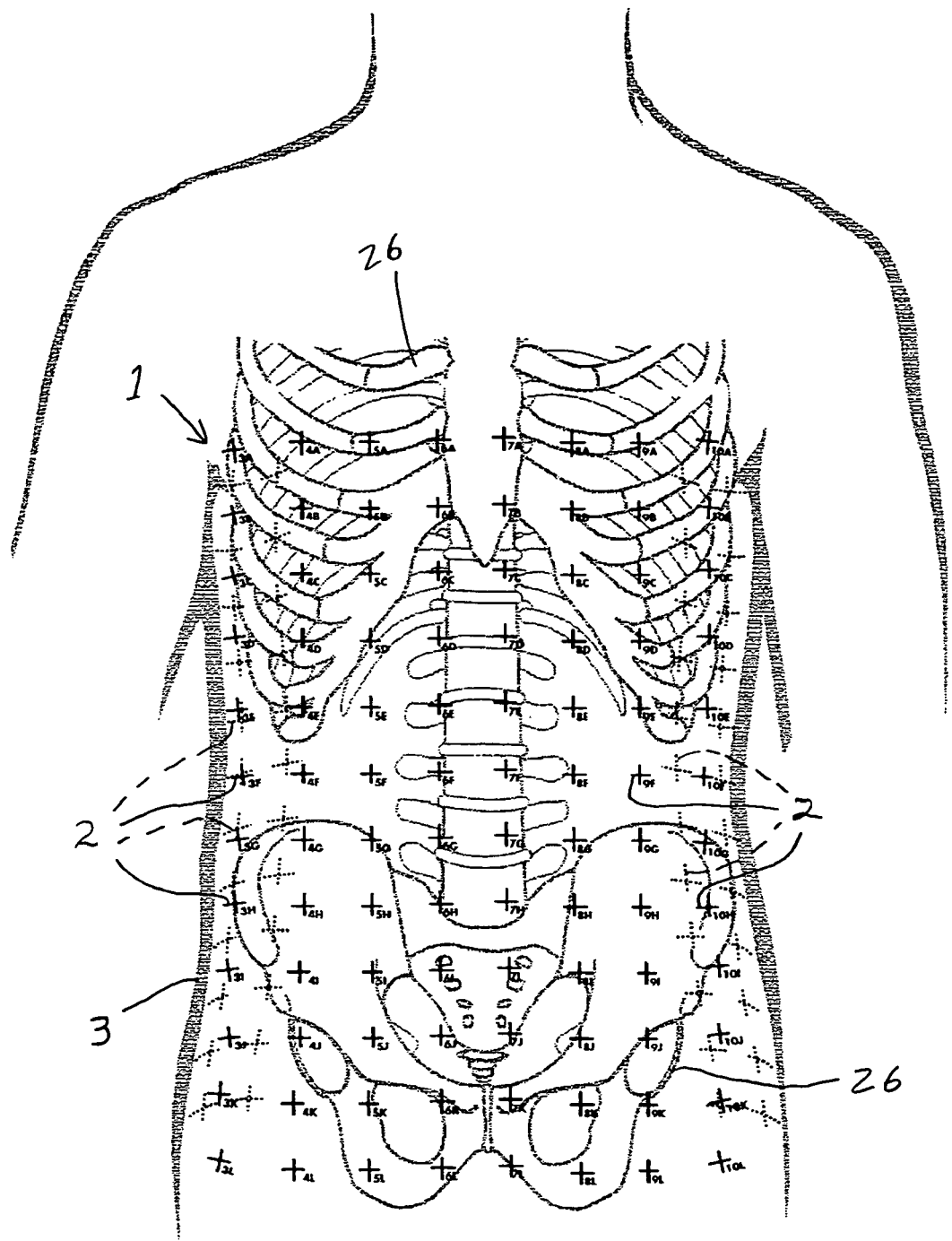
FIG. 2 is a view of a radiographic image of the torso of FIG. 1 with the surgical targeting grid and skeletal elements visible.

A surgical targeting system of the present invention, is designated generally by the reference numeral 1 in FIG. 1. The surgical targeting system 1 is used for adding an indicia image 2 to a radiographic image of a body 3 resulting from passage of image radiation through the body 4, as illustrated in FIG. 2.

The surgical targeting system 1 comprises an antimicrobial drape 9 having an inner surface 11 of sufficient flexibility to conform to at least a portion of the outer surface 6 of the body 4. The drape 9 comprises a plastic impregnated with iodophor. A preferred embodiment of the drape 9 is disclosed in the publication "3M® Ioban® 2 Antimicrobial Incise Drapes: Clinical Use Information" by 3M Health Care, the entire disclosure of which is hereby incorporated by reference herein. The inner surface 11 of the drape may be coated with an antiseptic. The drape 9 has an outer surface 14, and longitudinal and lateral edges 16, 19. The drape 9 is puncturable to provide access to the outer surface 6 of the body 4. The drape 9 is transparent to the imaging radiation.

The targeting system 1 further comprises an indicia 21 affixed to a portion of the drape 9. The indicia 21 are opaque to the imaging radiation resulting in the indicia image 2 corresponding to the indicia 21.

The targeting system further comprises a means for fixing the indicia 21 relative to the outer surface of the body 4 such that the indicia provide a reference on the body 4 for correlating portions of the body 4 to the radiographic body image 3. The fixing means may comprise adhesive 24 continuously applied to the entire inner surface 14 of the drape 9.

An emitter, such as an X-ray tube, and a receiver, such as an image intensifier, directed at one another in perpendicular relation to the plane of FIG. 1, may be employed to produce the image illustrated in FIG. 2. FIG. 2 includes indicia images 2 (corresponding to the indicia 21), a body image 3 (corresponding to the body 4), and a skeleton image 26.

Figure 3:
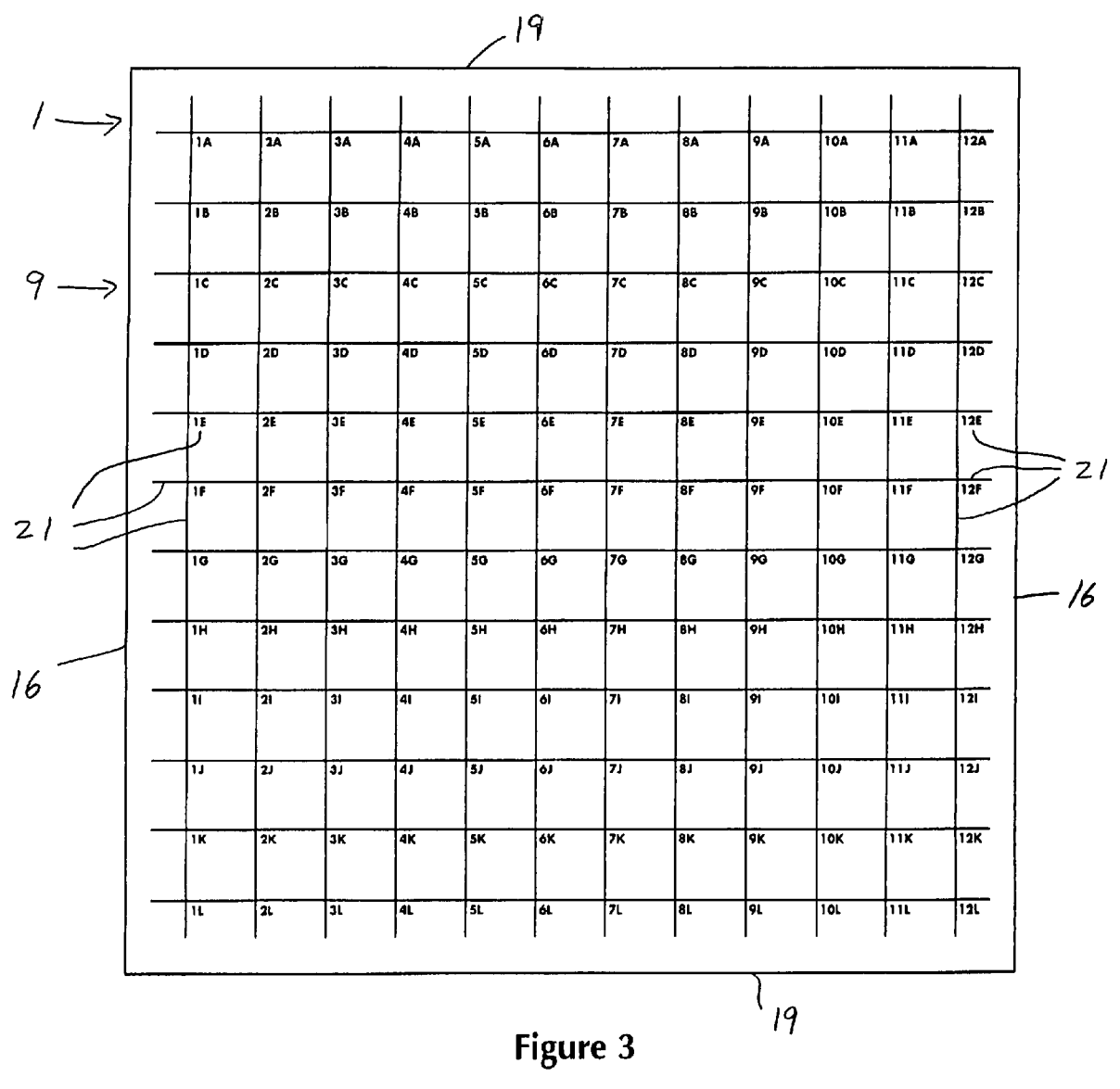
Figure 4:
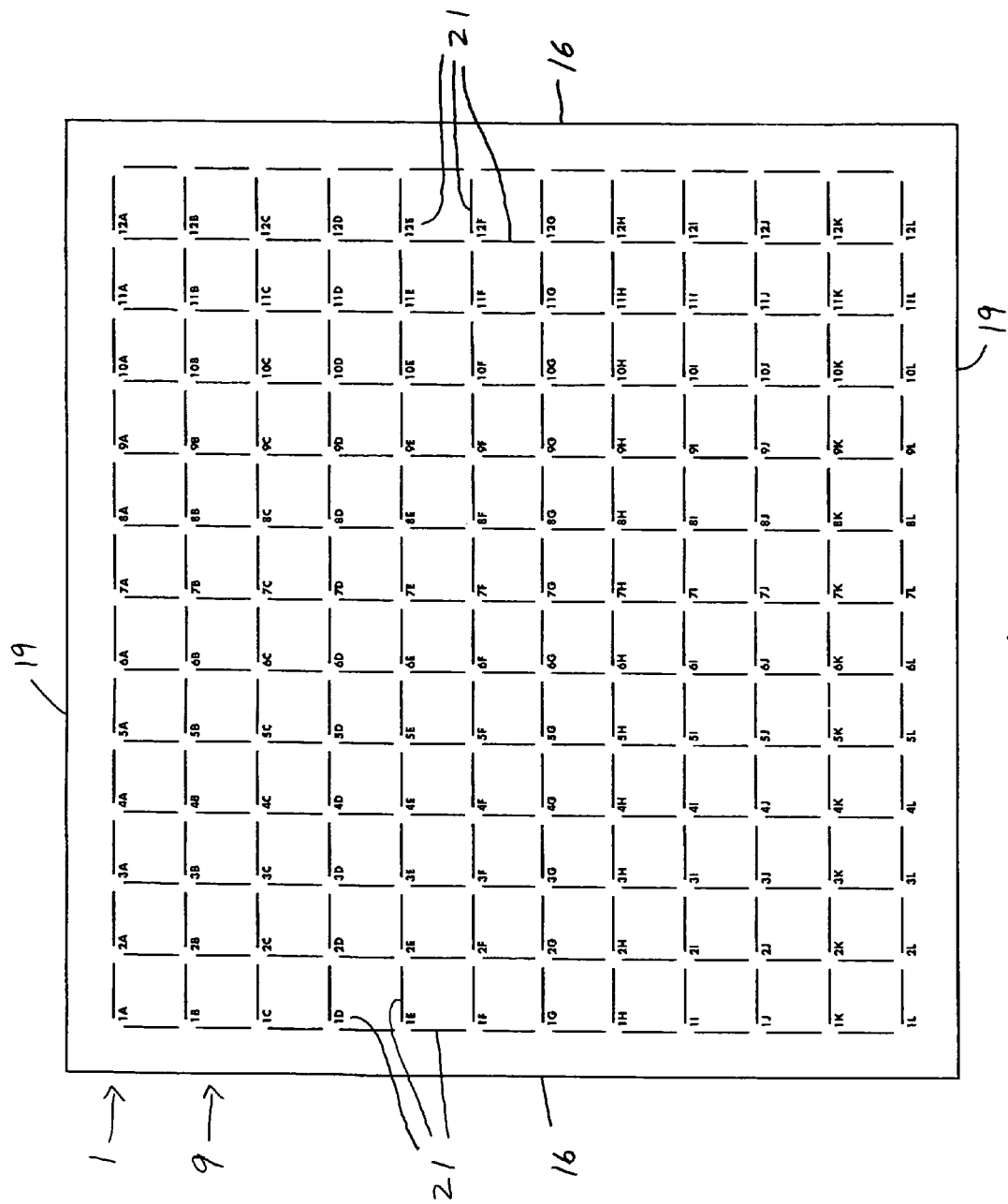
Figure 5:
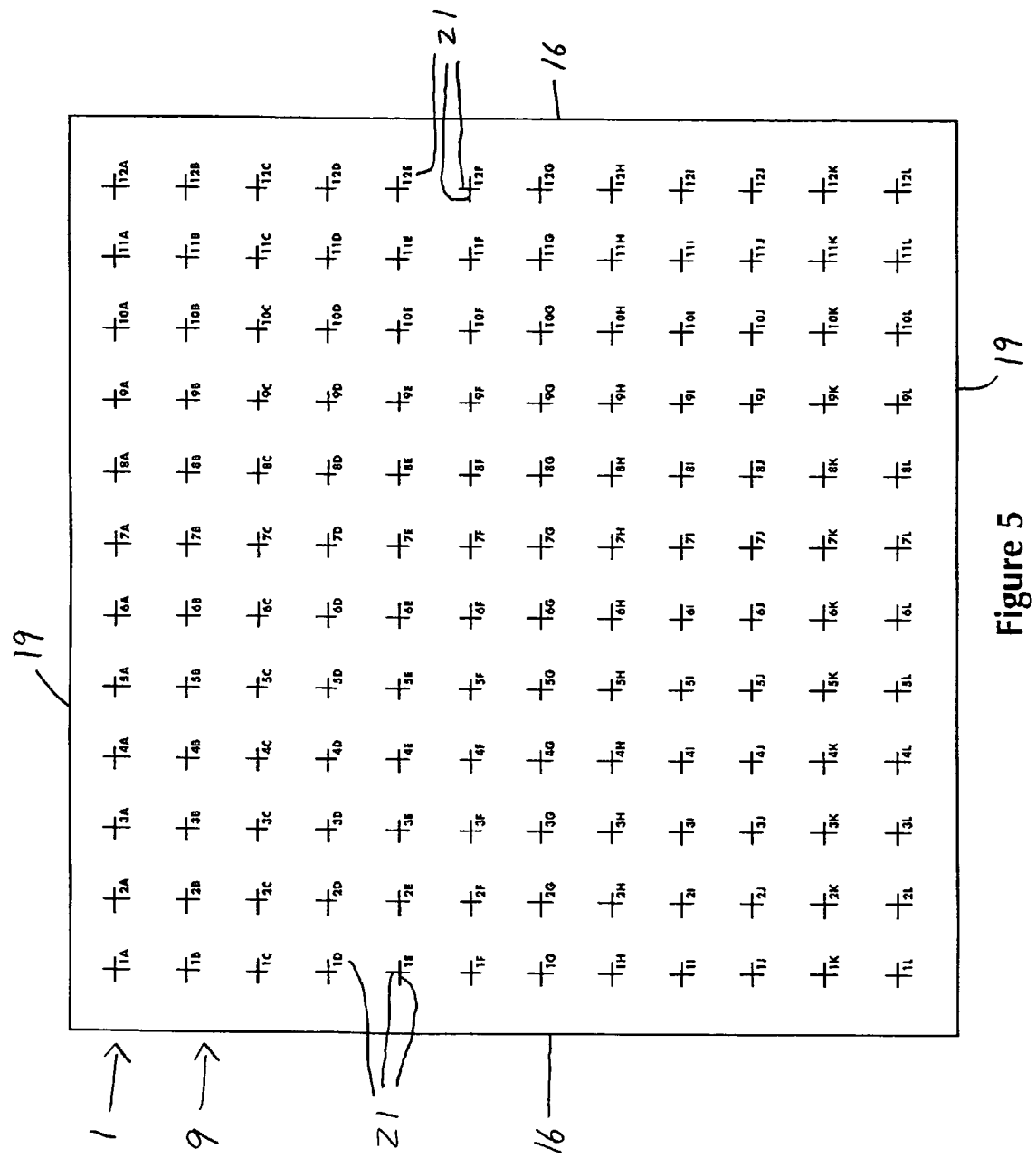

The indicia 21 may be constituted by various coordinate or grid systems such as are illustrated in FIGS. 3, 4 and 5. For a rectangular coordinate system, examples of which are shown in FIGS. 3, 4 and 5, the radiopaque medium forms two sets of thin lines. Each set of lines is parallel and equidistant to one another. One set of the lines is oriented 90° to the other to form a grid. The result is a pattern of radiopaque squares of equal size. These squares may range in size from 1 millimeter to a few centimeters across depending on the grid pattern needed for a specific application. The material comprising the lines must be such that the Ioban® drape material retains its flexibility so that it stretches over the complex curves of the human body. For instance, if the lines are composed of steel wires, each wire may be broken at every location where it crosses another wire as shown in FIG. 4. An alternative pattern which would fulfill this requirement would be the pattern shown in FIG. 5. In this manner, the segments of wire are free to move relative to each other, and the flexibility of the drape is not significantly compromised.

FIGS. 6, 7 and 8 illustrate an embodiment of the surgical targeting system 29 in which the surgical targeting system 1 is applied to anterior, lateral and posterior portions of the outer surface 34 of the chest or torso 31 of a body. The surgical targeting system 29 includes a drape 36 (corresponding to the drape 9), outer and inner surfaces 39, 41 (corresponding to the outer and inner surfaces 11, 14), and longitudinal and lateral edges 44, 46 (corresponding to the longitudinal and lateral edges 16, 19). The surgical targeting system 29 also includes indicia 56 (corresponding to the indicia 21) and adhesive 59 (corresponding to the adhesive 24). The drape 36, as applied to the torso 31, has anterior, lateral and posterior portions 49, 51, 54, as illustrated in FIGS. 6, 7 and 8.

Figure 10:
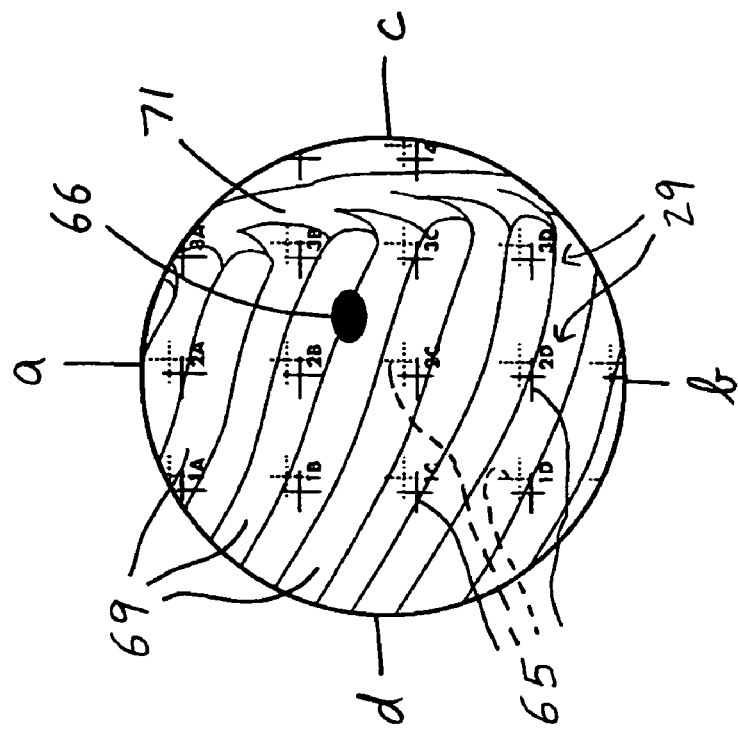
FIG. 10 is a view of a C-arm fluoroscopic image obtained from the apparatus depicted in FIG. 9.
Figure 9:
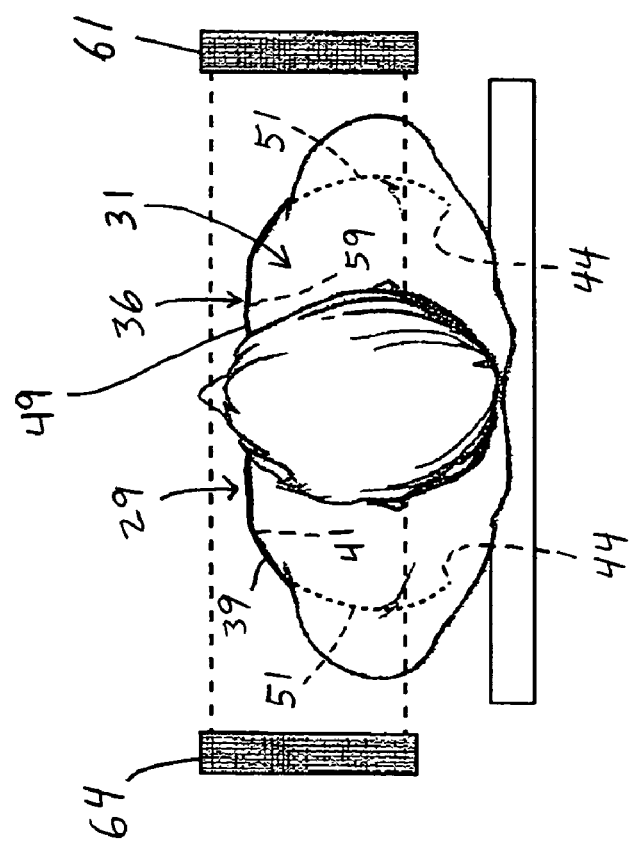
FIG. 9 is a superior view of the surgical targeting system of FIG. 6 with the patient lying on the operating room table from above with the emitter and receiving tubes of a C-arm fluoroscope depicted in position to obtain a lateral view of the targeted area.
Figure 12:
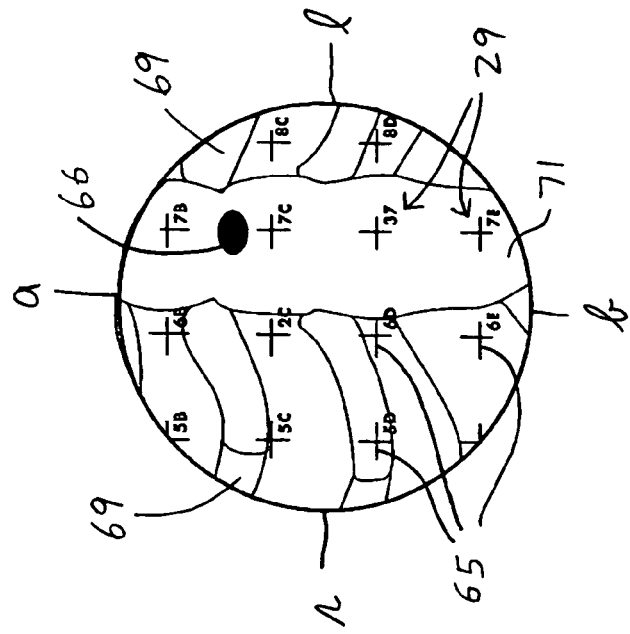
FIG. 12 is a view of a C-arm fluoroscopic image obtained from the apparatus depicted in FIG. 11.
Figure 11:
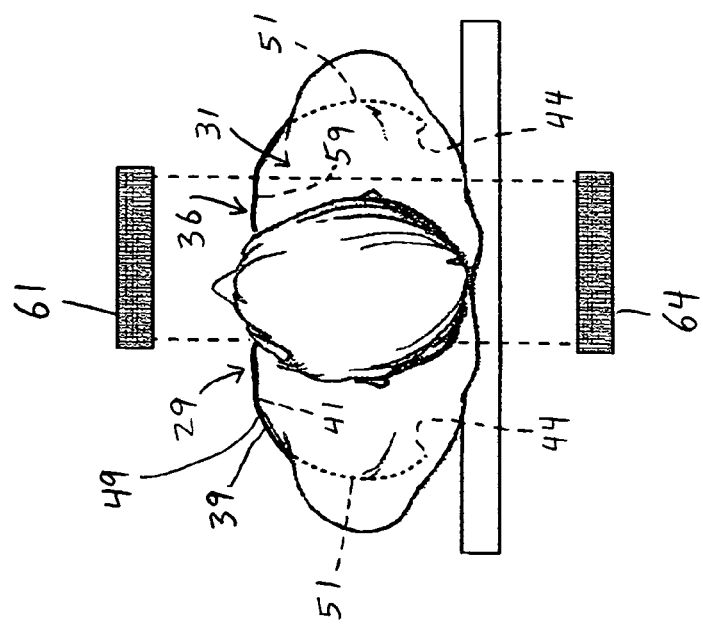
FIG. 11 is a superior view of the surgical targeting system of FIG. 6 with the patient lying on the operating room table from above with the emitter and receiving tubes of a C-arm fluoroscope depicted in position to obtain an anterior to posterior view of the targeted area.

An emitter 61, such as an X-ray tube, and a receiver 64, such as an image intensifier, arranged as shown in FIGS. 9 and 11, may be employed to produce the images illustrated in FIGS. 10 and 12, respectively. FIGS. 10 and 12 include indicia images 65 (corresponding to the indicia 56), a lesion image 66, rib images 69 and a sternum image 71.

The anatomical terms "superior" a and "inferior" b, with respect to the human body, refer to locations nearer to the head and to the feet of the body, respectively, relative to other locations. The anatomical terms "anterior" c and "posterior" d, with respect to the human body, refer to locations nearer to the front of and to the back of the body, respectively, relative to other locations. The term "lateral" refers to a location to the right or left sides of the body, relative to other locations. Alternatively, "lateral" refers to one or other side of the midline, with respect to the major axis of the body, or to a device lying in the major axis of the body. The term "medial" m refers to nearer to the mid-line. The left- and right-hand sides of the body are designated by the reference characters l and r, respectively.

Figure 14:
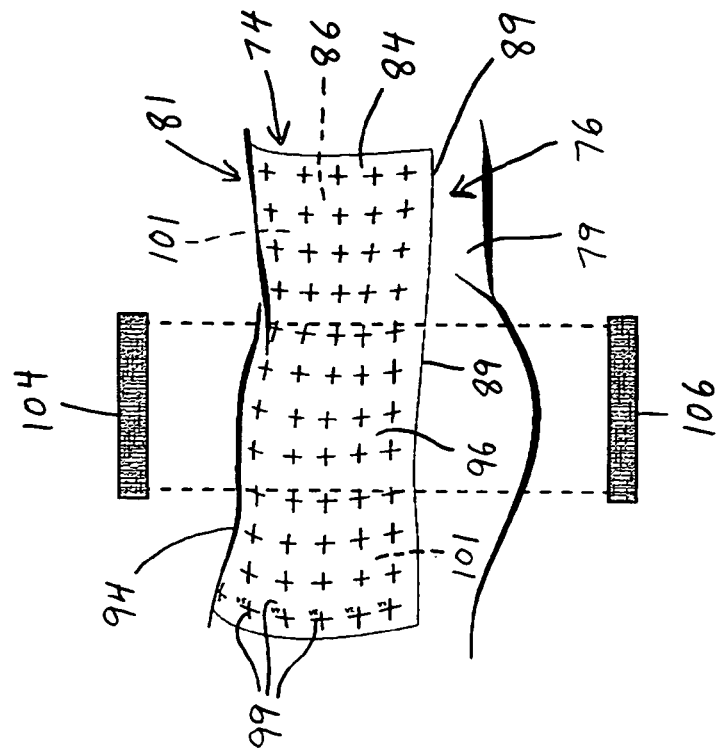
FIG. 14 is a lateral view of the surgical targeting system applied to the lower trunk of FIG. 13 from the lateral (side) aspect, the emitter and receiving tubes of a C-arm fluoroscope being depicted in position for an anteroposterior view of the targeted area.
Figure 13:
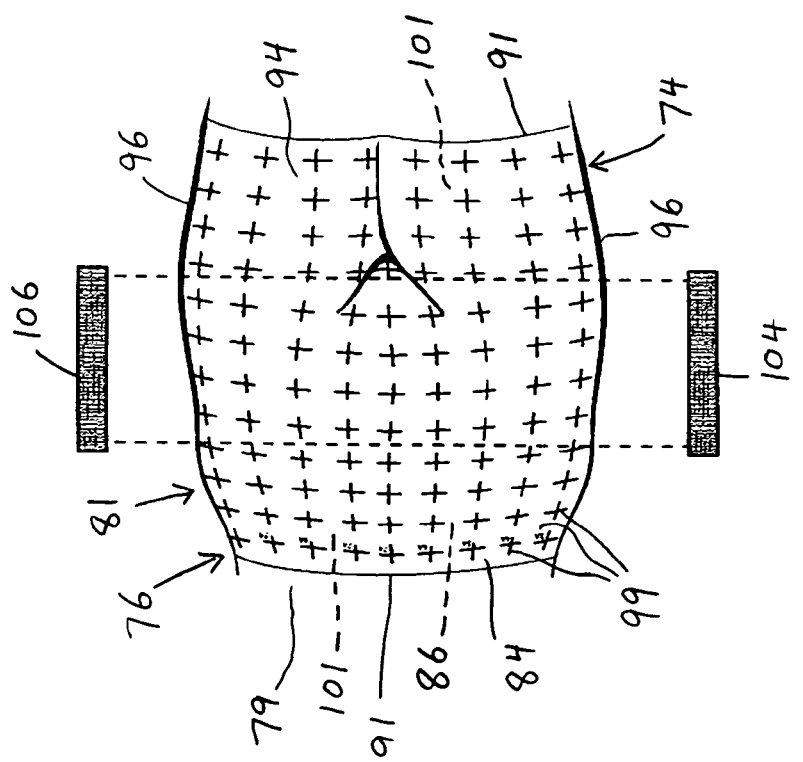
FIG. 13 is an anterior view of a lower trunk with the surgical targeting system of FIG. 1 applied to the anterior aspect as well as both sides, the emitter and receiving tubes of a C-arm fluoroscope being depicted in position for a lateral view of the targeted area.

FIGS. 13 and 14 illustrate an embodiment of the surgical targeting system 74 in which the surgical targeting system 1 is applied to anterior and lateral portions of the outer surface 79 of the lower trunk 76 of a body. The surgical targeting system 74 includes a drape 81 (corresponding to the drape 9), outer and inner surfaces 84, 86 (corresponding to the outer and inner surfaces 11, 14), and longitudinal and lateral edges 89, 91 (corresponding to the longitudinal and lateral edges 16, 19). The surgical targeting system 74 also includes indicia 99 (corresponding to the indicia 21) and adhesive 101 (corresponding to the adhesive 24). The drape 81, as applied to the lower trunk 76, has anterior and lateral portions 94, 96, as illustrated in FIGS. 13 and 14.

Figure 15:
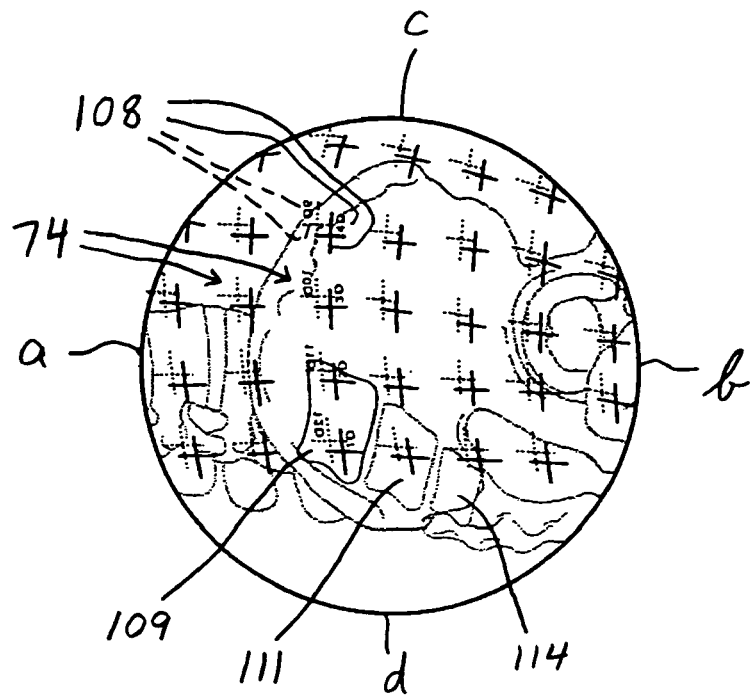
FIG. 15 is a view of the fluoroscopic image of the sacral elements and overlapping near and far surgical targeting grids obtained from the apparatus depicted in FIG. 13.
Figure 16:
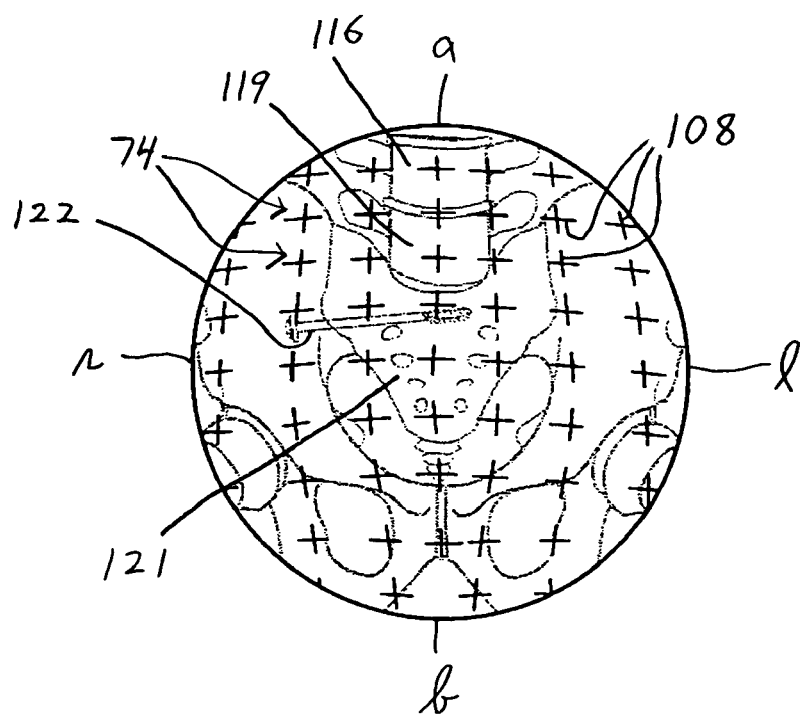
FIG. 16 is a view of the fluoroscopic view of the skeletal elements and overlying surgical targeting grid obtained from the apparatus depicted in FIG. 14, the position of an iliosacral screw used to address an unstable sacroiliac joint also being shown.
Figure 21:
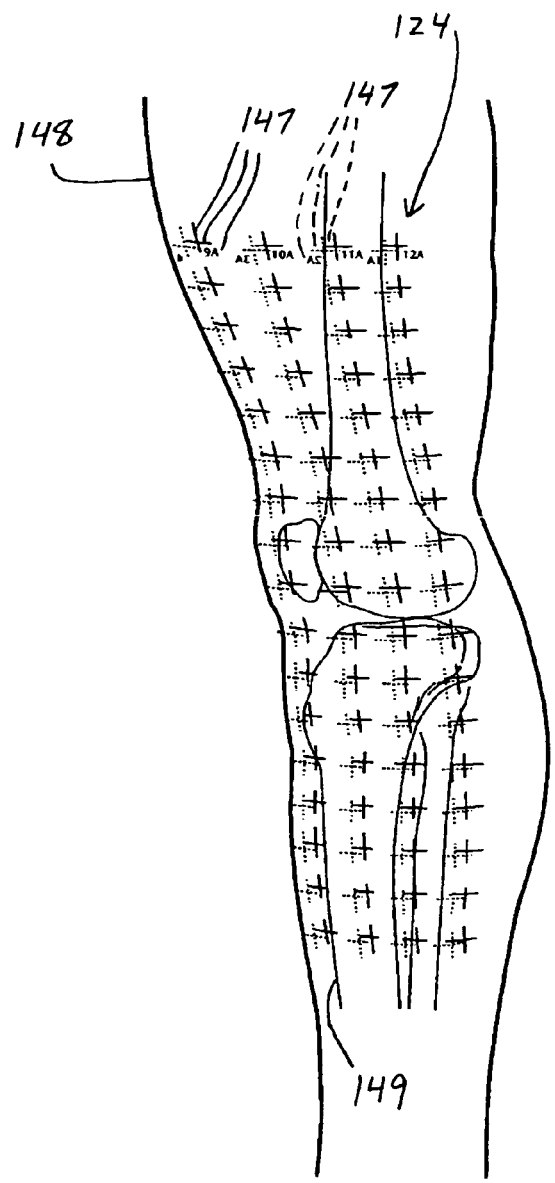
FIG. 21 is a view of a radiographic image of the skeletal elements and overlapping surgical targeting system of FIG. 17.
Figure 22:
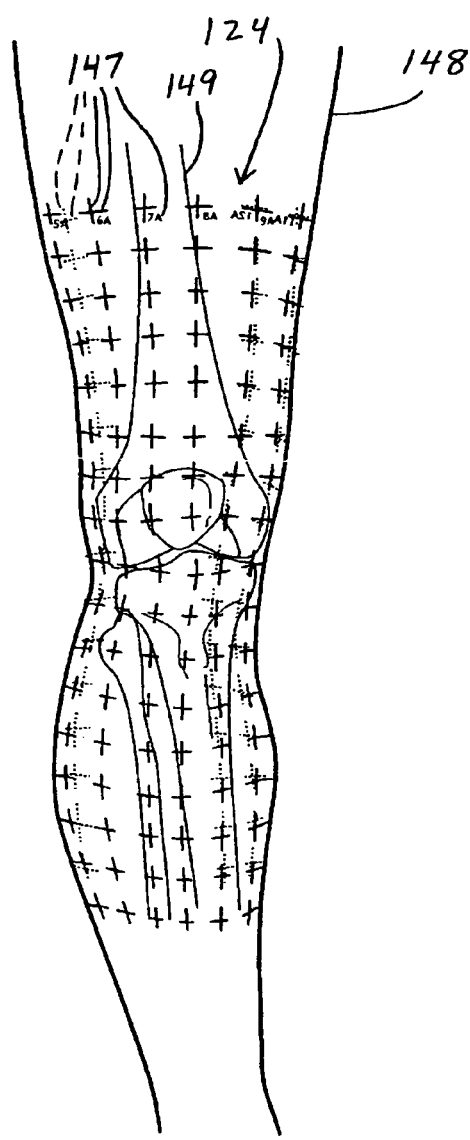
FIG. 22 is a view of a radiographic image of the skeletal elements and overlapping surgical targeting system of FIG. 18.

An emitter 104, such as an X-ray tube, and a receiver 106, such as an image intensifier, arranged as shown in FIGS. 13 and 14, may be employed to produce the images illustrated in FIGS. 15 and 16, respectively. FIGS. 15 and 16 include indicia images 108 (corresponding to the indicia 99), an S1 vertebrae image 109, an S2 vertebrae image 111, an S3 vertebrae image 114, an L4 vertebrae image 116, an L5 vertebrae image 119, a sacrum image 121, and a nail image 122.

FIGS. 17, 18, 19 and 20 illustrate an embodiment of the surgical targeting system 124 in which the surgical targeting system 1 is applied to the outer surface 129 of the lower limb 126 of a body. The surgical targeting system 124 includes a drape 131 (corresponding to the drape 9), outer and inner surfaces 134, 136 (corresponding to the outer and inner surfaces 11, 14), and longitudinal and lateral edges 139, 141 (corresponding to the longitudinal and lateral edges 16, 19). The surgical targeting system 124 also includes indicia 144 (corresponding to the indicia 21) and adhesive 146 (corresponding to the adhesive 24).

An emitter, such as an X-ray tube, and a receiver, such as an image intensifier, directed at one another in perpendicular relation to the planes of FIGS. 17, 18, 19, and 20, may be employed to produce the images illustrated in FIGS. 21, 22, 23 and 24, respectively. FIGS. 21, 22, 23 and 24 include indicia images 147 (corresponding to the indicia 144), a lower limb image 148 (corresponding to the lower limb 126), and bone images 149.

Figure 23:
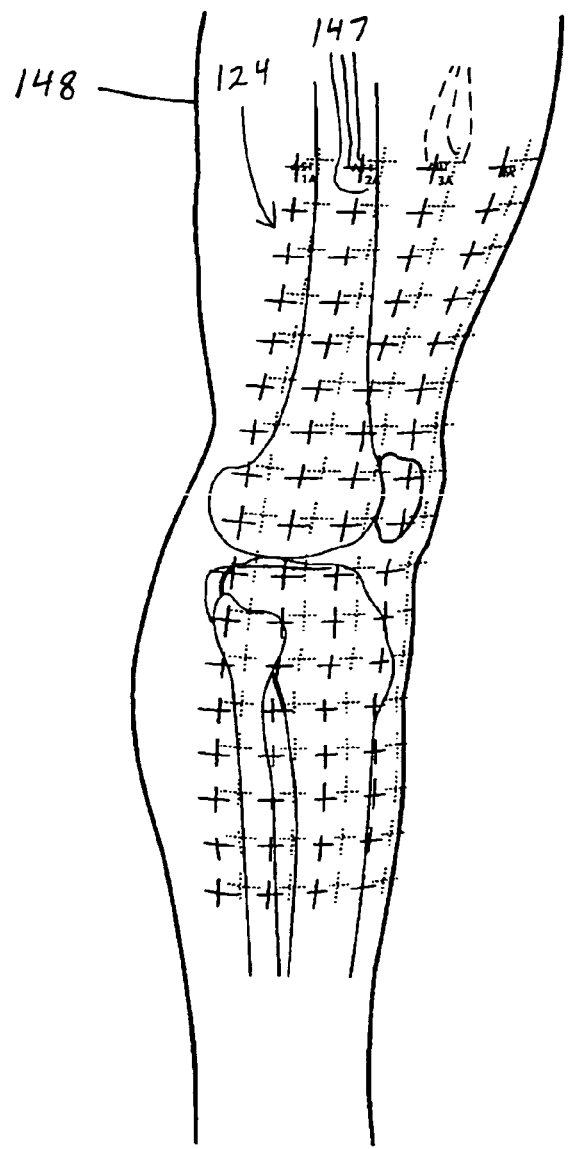
FIG. 23 is a view of a radiographic image of the skeletal elements and overlapping surgical targeting system of FIG. 19.
Figure 24:
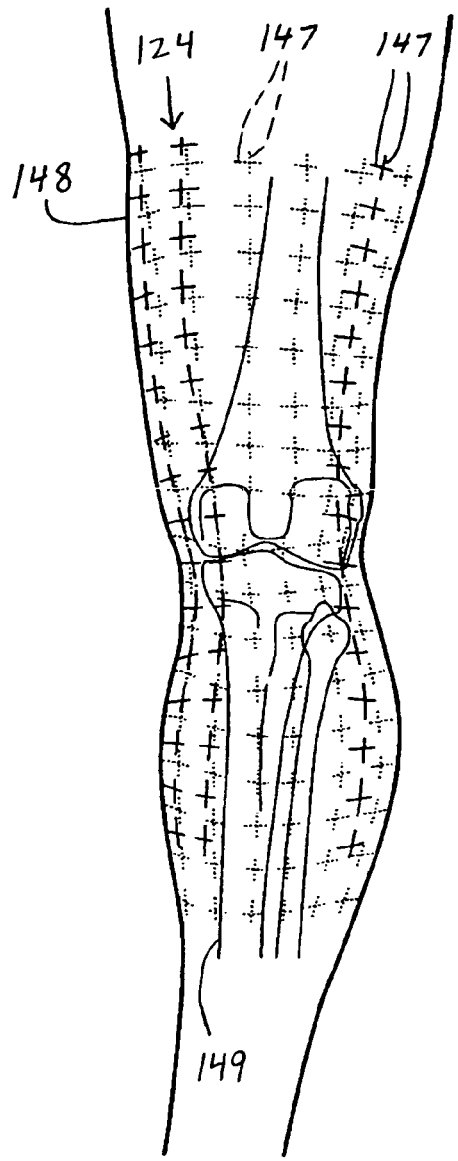
FIG. 24 is a view of a radiographic image of the skeletal elements and overlapping surgical targeting system of FIG. 20.
Figure 25:
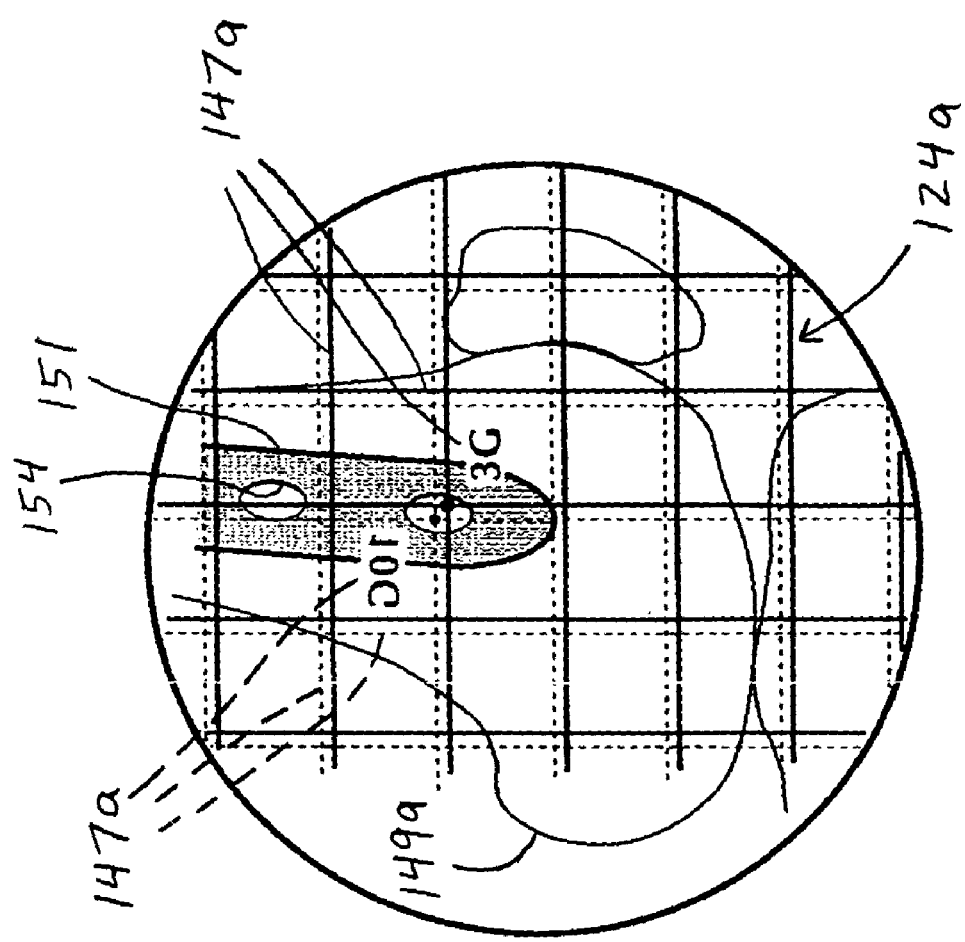
FIG. 25 is a C-arm fluoroscopic view of the distal femur from the lateral (or medial) aspect with the overlapping surgical targeting system of FIG. 23, targeting of the holes in the distal portion of a femoral intramedullary nail being facilitated by the near and far grid coordinates in the target nail hole such that with the grid properly positioned, these coordinates are directly read on the skin surface.

FIG. 25 is a view corresponding to FIG. 23. Accordingly, images in FIG. 10 corresponding to images in FIGS. 23 have the same reference numeral with the addition of the suffix a. FIG. 25 contains a nail image 151 of a femoral intramedullary nail having hole images 154. The indicia images 144a labeled "3G" and "10G" are shown positioned such that an axis intersecting these indicia images extends through one of the hole images 154 to facilitate location of the one hole in the intramedullary nail.

Figure 26:
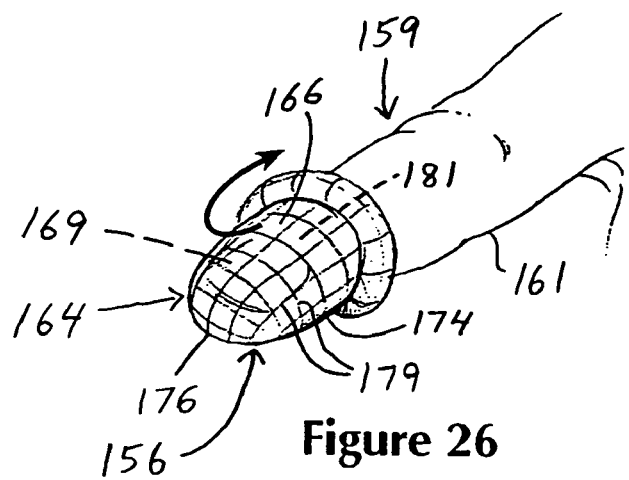
FIG. 26 is a perspective view of an alternative embodiment of the surgical targeting system of FIG. 1 applied to a digit (finger depicted), the rolled closed tube being capable of being unrolled from the tip of the digit.
Figure 27:
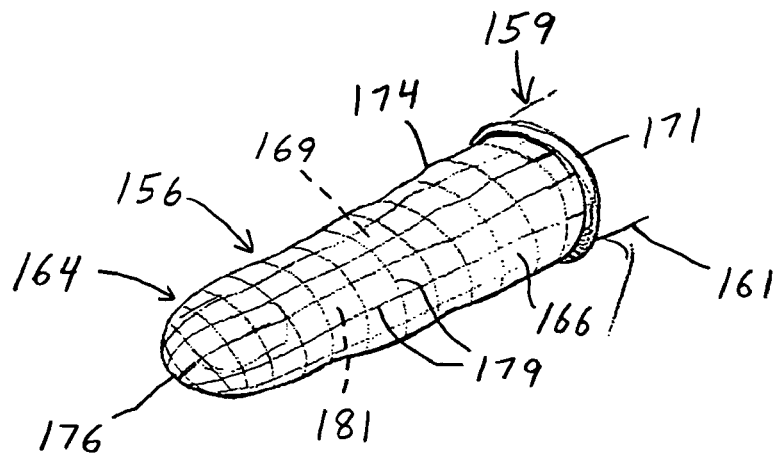
FIG. 27 is a perspective view of the surgical targeting system of FIG. 26, the rolled closed tube being unrolled further toward the base of the digit.

FIGS. 26 and 27 illustrate an embodiment of the surgical targeting system 156 for application to the outer surface 161 of an elongate portion of a body such as finger 159. The surgical targeting system 156 includes a drape 164 of similar material as the drape 9. The drape 164 has an inner surface 169 which, like the inner surface 14 of the drape 9, may be coated with an antiseptic. The surgical targeting system 156 has indicia 179 similar to the indicia 21.

The drape 164 has a cylindrical portion 174, one end of which is closed by a connected hemispherical end portion 176. The opposite end of the cylindrical portion 174 is defined by a rim 171. Prior to application to the finger 159, the drape 164 is rolled onto itself as shown in FIG. 26. The drape 164 is then applied to the end of the finger 159, as shown in FIG. 26, and unrolled to cover the finger as shown in FIG. 27.

The surgical targeting system 156 includes means for fixing the indicia 21 relative to the outer surface 161 of the finger 159, similar to the fixing means of the surgical targeting system 1. Accordingly, adhesive 181 may be continuously applied to the entire inner surface 169 of the drape 164. Alternatively, or in addition to the adhesive 181, the drape 164 may be fixed to the outer surface 161 of the finger 159 by forming the drape of expandable material and sizing it to have an internal volume which is less than the volume of the finger such that the drape is shrink-fitted onto the finger.

Figure 28:
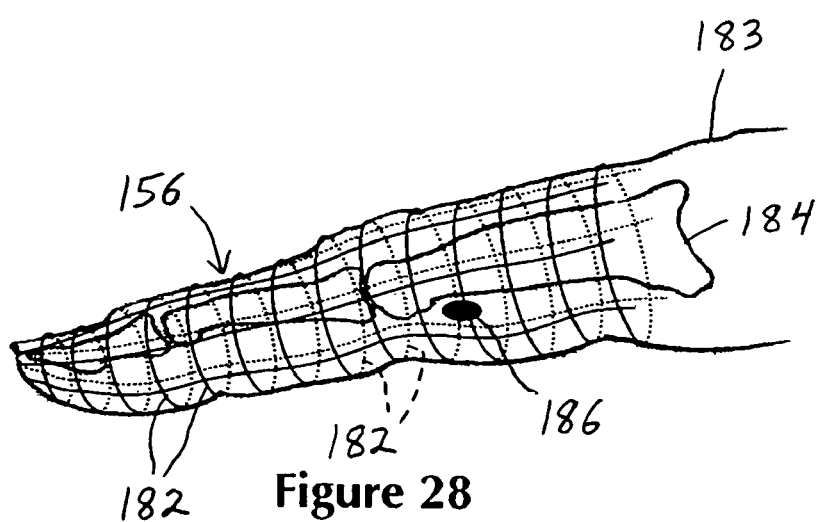
FIG. 28 is a view of a radiographic image of the digit and overlying surgical targeting system of FIG. 27 illustrating the skeletal elements of the digit.

An emitter, such as an X-ray tube, and a receiver, such as an image intensifier, directed in side elevation toward the surgical targeting system 156 as applied to the finger 159 in FIG. 27 may be employed to produce the image illustrated in FIG. 28. FIG. 28 includes indicia images 182 (corresponding to the indicia 179), a finger image 183 (corresponding to the finger 159), bone images 184, and a fragment image 186, such as may result from insertion of a foreign body into the finger.

Figure 29:
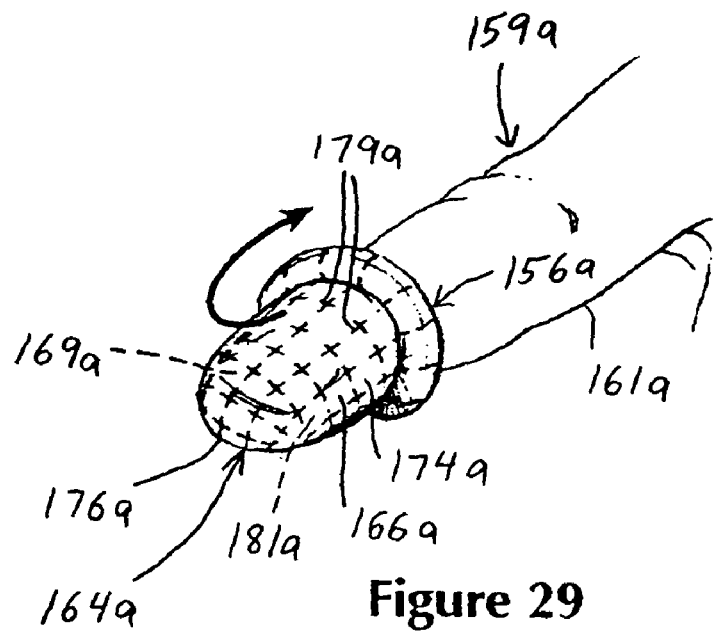
FIG. 29 is a perspective view of an alternative embodiment of the surgical targeting system of FIG. 26.
Figure 30:
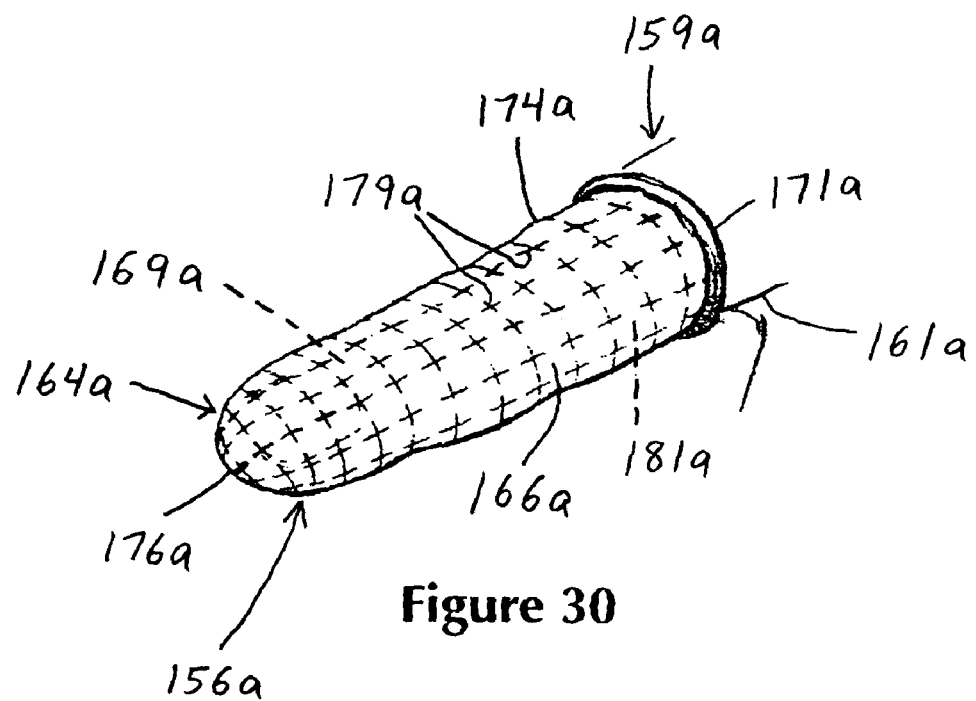
FIG. 30 is a perspective view of the surgical targeting system of FIG. 29 illustrating the rolled closed tube unrolled further toward the base of the digit.

FIGS. 29 and 30 illustrate a surgical targeting system 156a which is an alternative embodiment of the surgical targeting system depicted in FIGS. 26 and 27. Accordingly, structures in FIGS. 29 and 30 corresponding to structures in FIGS. 26 and 27 have the same reference numeral with the addition of the suffix a. The indicia 179a of the surgical targeting system 156a have the shape of "+" in contrast to the indicia 179 which are continuous.

Figure 31:
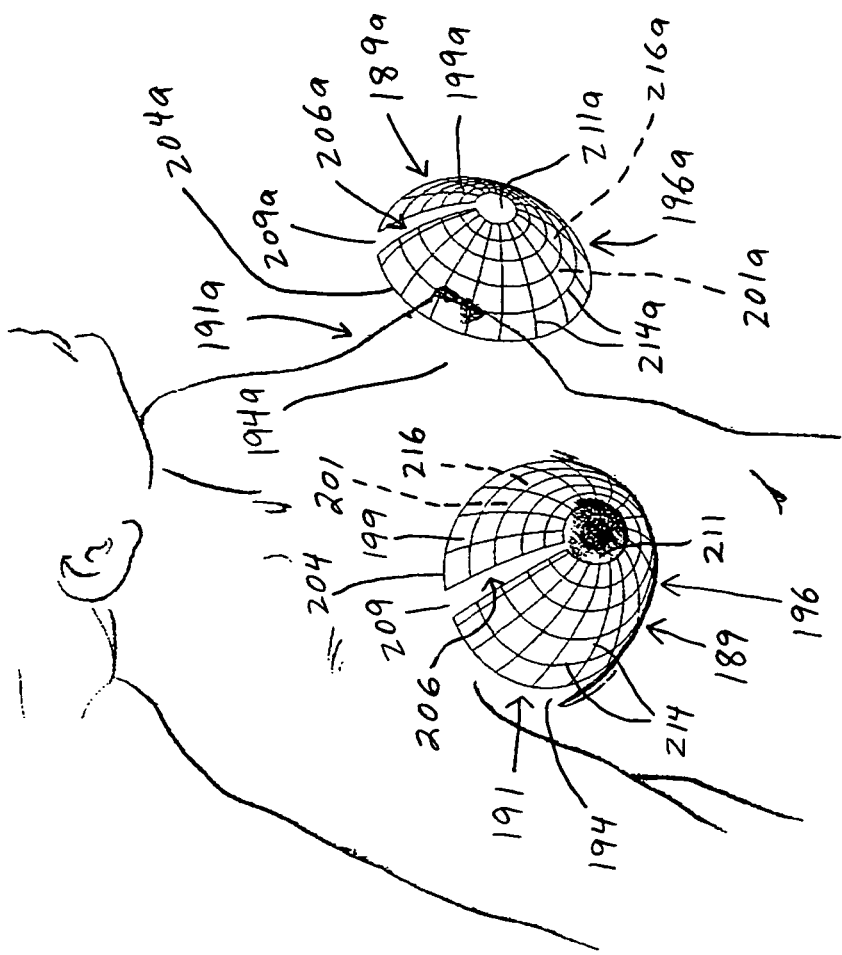
FIG. 31 is a perspective view of an alternative embodiment of the surgical targeting system of FIG. 1 for application to a human breast, the surgical targeting system including a cone-shaped drape with a cutout having an aperture in the center corresponding to the nipple of the breast.
Figure 32:
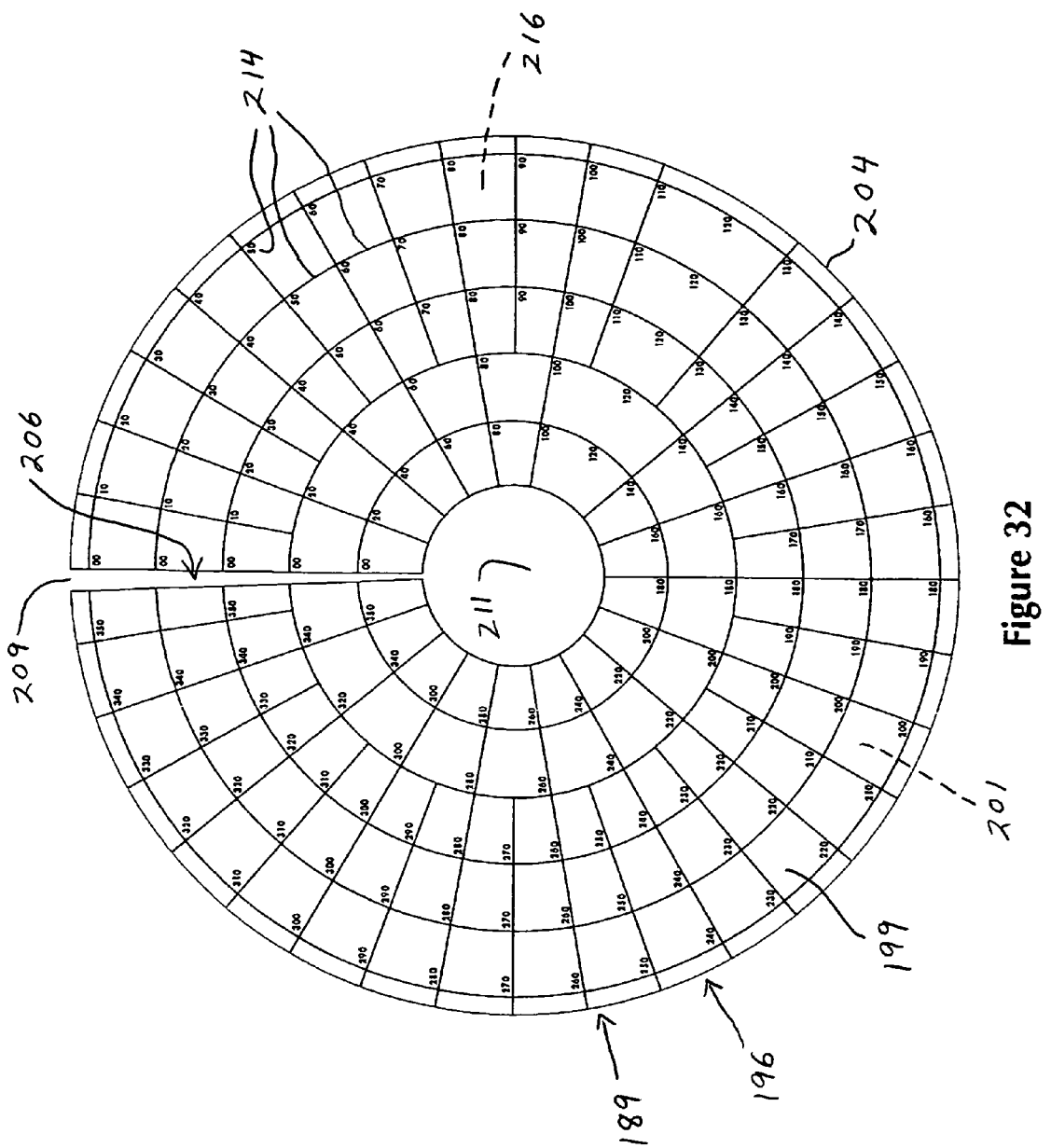
FIG. 32 is an anterior view of the surgical targeting system of FIG. 31 showing the surgical grid as a polar coordinate system.

FIGS. 31 and 32 illustrate an embodiment of the surgical targeting system 189 for application to the outer surface 194 of a right breast 191 of a body. The surgical targeting system 189 includes a right drape 196 of similar material as the drape 9. The right drape 196 has an inner surface 201 which, like the inner surface 14 of the drape 9, may be coated with an antiseptic. The right drape 196 also has an outer surface 199.

The right drape 196 is conical and has a radial cutout 206. The cutout 206 has a base 209 which coincides with a peripheral edge 204 of the drape, and a central aperture 211.

The surgical targeting system 189 has indicia 214 similar to the indicia 21. The indicia 214 are preferably a system of polar coordinates having a center coinciding with the apex of the right drape 196, as shown in FIG. 32. The indicia 214 of the polar coordinate system shown of FIG. 32 may include a radiopaque medium forming two sets of thin lines. The first set of lines radiates from a common center. The second set of lines forms concentric circles whose center is coincident with the intersection of the radial lines. The spacing between the radial lines and concentric circles varies from drape to drape depending on the specific application of the drape as well as the size of the tissue to be targeted. Depending on the material chosen to make the lines, the lines may also have to be broken at the intersections, as described herein above for the rectangular coordinate system, to allow for optimal flexibility of the system. Alternatively, if added stiffness is desirable and a specific tissue is hypermobile and therefore less amenable to targeting, a "closed" wire system with thicker and stiffer wires may be preferred. Each line or intersection is also labeled in a manner analogous to the rectangular coordinate system. A common perceived use for a polar system is with radiographic images produced for a mammographic examination and biopsy.

The surgical targeting system 189 includes means for fixing the indicia 214 relative to the outer surface 194 of the right breast 191, similar to the fixing means of the surgical targeting system 1. Accordingly, an adhesive 216 is continuously applied to the entire inner surface 201 of the right drape 196.

FIG. 31 also illustrates a surgical targeting system 189a which is an alternative embodiment of the surgical targeting system 189. Accordingly, the structures of the surgical targeting system 189a corresponding to structures of the surgical targeting system 189 have the same reference numeral with the addition of the suffix a. The surgical targeting system 189a is for application to the outer surface 194a of a left breast 191a of the body.

Figure 33:
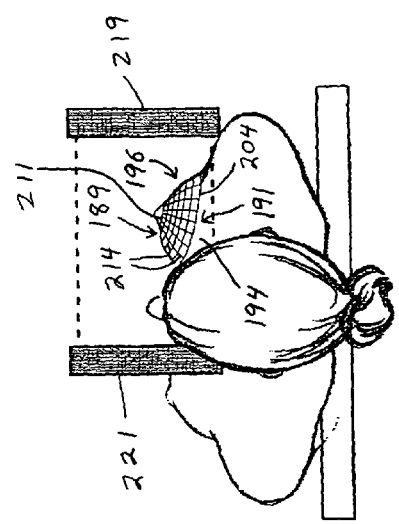
FIG. 33 is a superior view of a patient to whom the surgical targeting system of FIG. 31 is applied, the patient undergoing mammographic imaging where the emitter tube is medial and the receiving tube is lateral.
Figure 34:
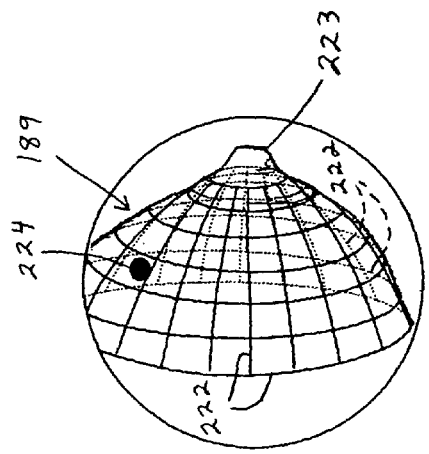
FIG. 34 is a view of the fluoroscopic mammographic image obtained from the apparatus depicted in FIG. 33 showing a lesion located cephalad, in line with the specific grid markings illustrated.
Figure 35:
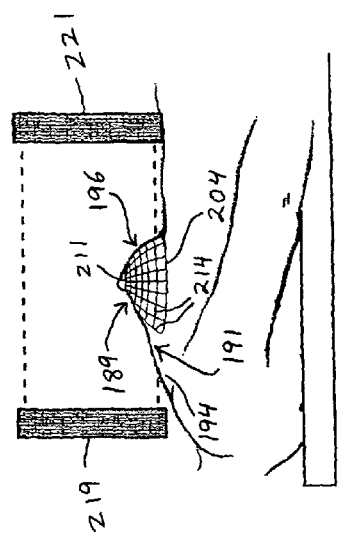
FIG. 35 is a lateral view of a patient to whom the surgical targeting system of FIG. 31 is applied, the patient undergoing mammographic imaging where the emitter tube is cephalad (above) and the receiver tube is caudad (below)
Figure 36:
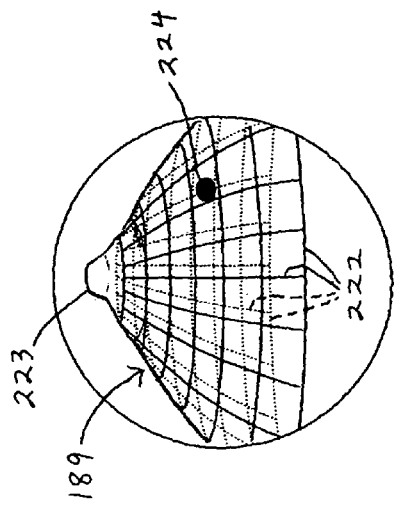
FIG. 36 is a view of the fluoroscopic mammographic image obtained from the apparatus depicted in FIG. 35 showing a lesion located laterally, in line with the specific grid markings illustrated.

An emitter 219, such as an X-ray tube, and a receiver 221, such as an image intensifier, arranged as shown in FIGS. 33 and 35, may be employed to produce the images illustrated in FIGS. 34 and 36, respectively. FIGS. 34 and 36 include an indicia image 222 (corresponding to the indicia 214), a right breast image 223 (corresponding to the right breast 191), and a lesion image 224.

Operation

As an example, a tumor in the mediastinum (the central portion of the chest cavity) may be localized and biopsied/resected (Depicted in the series of FIGS. 6, 7, 8, 9, 10, 11 and 12). Once the area of the body has been prepped and draped, the sterile pack of the grid system is opened and the grid system is removed. Using aseptic technique, the surgeon peels back the protective sheet of the grid system, exposing the adhesive backed sheet. This can then be applied to the area (now dry) for targeting as well as to secure the neighboring sterile towels and sheets. It is applied, adhesive side down, and pressed firmly in place. FIG. 6 shows a patient lying on a radiolucent operating room table with the surgical targeting grid being applied to the sides and anterior aspect of the chest wall, covering the area where the lesion is known to be. FIG. 7 shows the view of the upper torso of this patient from the side view with the emitter and receiver tubes of the C-arm fluoroscope also depicted in position for an anteroposterior view of the targeted area. FIG. 8 shows the view of the upper torso of this same patient from the anterior (front) aspect with the surgical targeting system in place. The emitter and receiver tubes of the C-arm are depicted in position for a lateral view of the targeted area. FIG. 9 shows the same patient from the cephalad aspect with the emitter and receiver tubes in position for the lateral X-ray/ fluoroscopic image which is depicted in FIG. 10. FIG. 11 shows the same patient from the cephalad aspect with the emitter and receiver tubes in position for the anteroposterior X-ray/fluoroscopic image which is shown in FIG. 12.

Another example is as an aid in the accomplishment of accurate placement of an iliosacral screw for fixation of an unstable sacroiliac joint following trauma. FIG. 13 shows an oblique view of a patient lying on a radiolucent operating room table after suitable prepping and draping of the skin to create a sterile surgical field with the surgical targeting grid applied to the anterior and lateral aspects of the lower trunk (pelvic area). FIG. 14 shows this same patient from the lateral (side) view and emitter/receiving tubes as they would be positioned for an anteroposterior radiographic/fluoroscopic view. FIG. 15 is a view of the skeletal elements and overlapping near and far surgical targeting grids. Targeting in this instance can proceed from the near hatch mark which is superimposed on the center of the first sacral vertebral body to its nearly collocated counterpart on the far grid (See FIG. 15). FIG. 16 shows the skeletal elements on the anterior view. The depth as well as the angle of incidence of the pin or screw can be ascertained on this view. Subtle alterations in the angle of inclination of this guidewire are critical and it is safest (least likely to injure a nerve) if it is directed slightly cephalad and anterior. Knowing this, the operator may choose to set the collinear points by adjusting the angle of the incident beam of the fluoroscope just off the lateral, with the near grid point slightly posterior and caudad, the far grid point slightly anterior and cephalad. Simply reading the far and near coordinates overlapping the center of the first sacral body will then give the coordinates on the surface of the body which can then be used to aid targeting.

Targeting these points by way of instruments may be facilitated in several ways, including laser light beams from the emitting and receiving tubes on the C-arm fluoroscope directed parallel to the beam and targeted then at the specific target (near and far respectively) coordinates on the patient. Directionality of the pin or instrument or implant by keeping it exactly within beam of light would aid accurate placement. Alternatively, use may be made of a "C" guide (an instrument that directs the passage of a pin or drill from one point to emerge at a precise second point given by the instrument) where one point of the "C" is on the near target coordinate and the other point of the "C" on the far coordinate.

The surgical targeting grid may also be utilized on the limb to facilitate percutaneous targeting. FIGS. 17, 18, 19 and 20 show the surgical targeting grid applied around three quarters of the circumference of the lower thigh, knee, and upper leg with only the posterior portion of the leg not covered) FIGS. 21, 22, 23 and 24 show the corresponding skeletal elements and overlying surgical grids. Note that on the medial (FIG. 21) and lateral (FIG. 23) views, there are two grids seen, one near and the other on the far side. With a locking intramedullary nail in place within the femoral intramedullary canal, interlocking the nail (drilling a hole across the femur and through the hole in the nail, followed by the placement of a screw) can be facilitated by precise targeting utilizing the near and far hatch marks at the center of the target—in this case the circle which represents the hole in the intramedullary nail.

Targeting the coordinates can be done by using the surface coordinates as described for the iliosacral screw fixation.

Another example is provided by locating a retained foreign body in a finger. FIGS. 26 and 27 show the adaptation of the surgical targeting grid for placement on a digit, with FIG. 26 showing the system partially and FIG. 27 showing the system fully unfurled. FIG. 28 shows the skeletal elements on a lateral roentgenographic/fluoroscopic view with a foreign body. By obtaining an X-ray or C-arm view at right angles to this one, i.e., in the anteroposterior view, the foreign body can be precisely located and extracted with an incision centered at the appropriate location given by the surface coordinates. FIGS. 29 and 30 show an alternative construct of the surgical targeting grid for this application being applied to the digit.

Another example of the surgical targeting system would be for mammographic biopsy. For this application, the adaptation of the surgical grid system is shown in FIG. 32 where a polar coordinate system is used, i.e., a series of concentric lines at regular intervals are intersected by a series of lines perpendicular to them and converging on the center. The system is cone shaped, to conform to the shape of the breast with a slit and an open center to accommodate different sizes. FIG. 33 shows the patient from the cranial (top) view with the emitting and receiving tubes inside (medial) and outside (lateral) the breast which is to be imaged after the skin has been prepped appropriately and a surgical field created with appropriate draping, and the surgical targeting system applied. FIG. 34 shows a roentgenographic/fluoroscopic view of the breast with the overlapping surgical targeting system in place and a lesion visible. FIG. 35 shows a side (from lateral) view of this same patient's breast with the emitter/receiving tubes cephalad (up or toward the head) and caudad (down or toward the feet) and FIG. 36 shows the corresponding roentgenographic/fluoroscopic view with the lesion and overlapping surgical grid. By advancing the biopsy needle/trocar from the appropriate coordinates on the surface of the breast (FIG. 34) to the depth as designated on the view at right angles to it (FIG. 36), a more precise localization with fewer "passes" and less irradiation exposure of patient and operator can be achieved.

Another example somewhat analogous to the former is provided by the process that is utilized when finding the correct start point on the outer distal femur for interlocking nailing (with the modification of depth assessment—where the second view is often obtained to verify screw length) and applies to circumstances where the instrument or implant is to be advanced "end on" the target tissue and parallel to the direction of the fluoroscopic or roentgenographic beam. In instances where this is not the case, e.g., when the start point for an intramedullary nailing on the skin needs to be determined, knowing that this position on the skin must be collinear with the proximal femoral shaft, the assessment of colinearity can be accomplished by applying the surgical targeting grid so that it is collinear with the proximal femur on the lateral aspect (this may require C-arm fluoroscopic X-ray check during the act of grid placement, with extension of the placement cephalad as far as the buttock) as well placement of a second grid on the anterior aspect with extension cephalad as far as the buttock—at which point it overlaps the first surgical targeting system. By noting which grid row overlies the proximal femoral canal on the anteroposterior projection and also noting which grid row from the second surgical targeting system overlies the proximal femoral canal on the lateral projection, the start point on the skin is given by the intersection of these two rows on the surface of the buttock area. This is of special importance in percutaneous intramedullary nailing procedures, where the selection of an incision point which is not collinear with the proximal femur may cause tenting a large cuff of soft tissue during the procedure and may necessitate extension of a small incision. Finding this point on the skin might otherwise entail multiple fluoroscopic X-ray views, each of which impart radiation exposure to the patient as well as the surgeon and other operating room personnel. An additional point is that accurate location of this point permits a small skin incision and this, with healing becomes a small scar which, if later extraction of the device is opted for, facilitates the accomplishment of the procedure, again, as a percutaneous one (with a limited incision whose locus is given by the existing scar).

Another example of the utility of the system is provided by the procedure of reamed femoral intramedullary nailing. When the currently commonly utilized process (using an overlying radiopaque object to find a locus on the skin as described in the section titled "Background of the Invention") is used to monitor the passage of a surgical instrument down a surgical corridor, multiple additional fluoroscopic views may be needed. An example of this would be passage of a guidewire down an intramedullary canal for a fracture of the femur. Knowing which direction to point the angled tip of the guidewire entails knowing which direction the fragment on the other side of the fracture is displaced. Additional spot fluoroscopic views of the fracture with an overlying radiopaque object (such as a hemostat) gives the needed answer and prompts the surgeon to rotate the guidewire so that its tip is toward the intramedullary canal on the displaced fragment before advancing the wire down the fragment's canal. With a surgical targeting device in place, obtaining additional fluoroscopic X-rays for this purpose are unnecessary. The added advantageous factor is that the surgeon need not place his hand near the radiation beam with the surgical instrument which is an occupational hazzard for many surgeons. Additionally, minor directional adjustments in the passage of a radiopaque instrument or implant in the body can be subject to less guesswork because both the coordinates on the fluoroscopic screen and those directly readable on the patient can be correlated. "Guesswork" however may prompt the operator to take more fluoroscopic X-rays or may result in the need for several passes through the patient's tissues with the instrument or implant before the correct corridor is secured. Having an in place targeting system, therefore, may provide the surgeon with a series of constant reference points throughout the entirety of the procedure. Having these will facilitate the accuracy and speed of the procedure and diminish the potential hazzard to the patient (additional radiation exposure and damage to tissues from inaccurate passage of instruments or implants under fluoroscopic control) as well as to the surgeon and the operating room personnel (radiation exposure—both generally and locally to the surgeon's hand).

Procedures which may utilize the surgical targeting system of the present invention include:

Percutaneous and limited skin incision surgical procedures that are reliant, either totally or partially on guidance from fluoroscopic or conventional X-ray guidance;

Bone fixation;

Biopsy needle/trocar placement;

Bone graft trocar placement;

Bone graft substitute trocar placement;

Localization of gantries for radiation therapy, and placement of radioactive sources for this purpose;

As an aid to the precise direction of electromagnetic radiation, sonic waves directed either singly at an individual target or from multiple projections at a single target;

Locating a foreign object or foreign objects;

Extracting or manipulating these foreign objects percutaneously;

Localization of tracts (e.g, sinus tract infection);

Positioning of ultrasonic or magnetic field stimulation in relation to bone/soft tissue fixation;

Wire and pin placements for cannulated screw fixation and accurate bone anchoring;

Manipulation/removal/repositioning of existing implants;

As an aid to the accomplishment of percutaneous procedures;

As a means of cross checking computer guided or computer assisted surgery Intracranial targeting;

As an aid in biopsying/staging gastrointestinal/urinary tract tumors (in combination with endoscopic findings—the surgical targeting grid can be used to locate the tip of the endoscope, and thereupon direct the tip of a laparoscope to visualize the outside wall of the viscus for the purpose of staging/biopsy);

As an aid in directing the placement of a mediastinal scope;

As an aid in determining the position of a bronchoscope; and

Placement of other implants or reservoirs.

Alternative embodiments of the invention are possible, in addition to integrating this grid system into a sterile drape. For example, other methods of surgical targeting may be employed by combining a sterile radiopaque grid with a removable glove or sock or a condom for the extremity, finger or other appendage. Such a device is stretchable with enough friction to minimize any shearing between it and the skin and may not require adhesive backing or perhaps only minimal adhesive backing. This device would allow for surgical targeting of the upper and lower extremities. Another embodiment would be that applicable to the breast, i.e., a polar coordinate grid system on a conically shaped sterile plastic adhesive drape with the central portion for the nipple cut out and a slit to permit size adjustment.

By disposing the system around the lower trunk, starting from one lateral side, across the anterior aspect and over the opposite lateral side, the use of parallax by superimposing grids or grids disposed at right angles to each other can be used to find the relation of a locus to the surface coordinates as well as in directing the angle of entry and depth of penetration of the surgical instrument or implant by the operator.

In summary, the surgical targeting system of the present invention includes a surgical adhesive drape (which is form-fit to a specific body part such as a digit, with no possibility for shearing between the skin and the overlying grid) which is transparent or translucent and radiolucent excepting the indicia of the surgical targeting system which are radiopaque and clearly visible both directly and on a radiographic/fluoroscopic image. Additionally, the drape is impervious to moisture and bacteria and has an option for inclusion of an uniformly distributed topical antiseptic on the surface of the drape which is applied to the body. The surgical targeting system includes one or several patterns of radiopaque lines disposed at right angles to each other and each with distinguishing radiopaque labels. Both the lines and the labels are easily readable both on fluoroscopic views as well as directly once the targeting systems have applied to the surface of the body.

Simultaneous application of the drape (or separate drapes) to "near" and "far" body surfaces enables the surgeon to take advantage of parallax and utilize both surgical grids for precise direction of a surgical tool or implant such as a needle, drill, pin, rod, biopsy tool or trocar. Similarly, by locating two grids over the body area of interest at right angles to each other, one grid can be used to isolate a starting point and the second grid can be utilized with fluoroscopic views also at right angles to the overlying second grid to control the depth and angle of inclination of the inserted instrument or implant. This feature of parallax can also be utilized in the instance of overlapping (near and far) grids, disposed on opposite sides of the body or body part by assuring co-linearity of the target with far and near grid points. Subtle adjustments in the angle of the radiographic/fluoroscopic beam result in changes in the collinear near and far coordinates.

Once the desired coordinates for passage of the instrument or implant are known, several strategies incorporating the grid coordinates can then be used to assist targeting. One strategy for the accomplishment of this would entail a visible light beam projection from the middle of the C-arm fluoroscope from both the emitting and receiving elements, directed by the operator to the corresponding near and far target grid points on the skin. Another strategy would entail the use of a "C" targeting device as previously described.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

The invention claimed is:

1. A method for correlating the buttock with the femoral canal of the femur of a body, said method comprising the steps of:

applying a radio-transparent drape having at least two indicia each comprising a radio-opaque longitudinal axis to the leg of the body such that a first portion of the drape extends in an anterior-posterior plane relative to the body, said applying step further providing for a second portion of the drape to extend laterally relative to the body, said applying step providing further for each of the indicia to be contained in respective first and second portions of the drape, said applying step providing further for each of the indicia to be longitudinally and centrally aligned relative to the leg;

directing imaging radiation through said drape such that a radiographic image of said body and indicia is formed on a medium;

comparing, by viewing the radiographic image, the relative positions of each of the indicia relative to the longitudinal axis of the femoral canal;

translating the drape, as required, relative to the leg such that one of the indicias is contained in an anterior-posterior plane which coincides with the longitudinal axis of the femoral canal, and such that the other of the indicia is contained in a lateral plane which coincides with the longitudinal axis of the femoral canal; and locating the intersection of the indicia on the buttock, the intersection of the indicia defining a start point for a reference axis which, when intersecting said start point and parallel to the indicia, coincides with the longitudinal axis of the femoral canal.

2. A method as set forth in claim 1 and further comprising the steps of:

positioning a longitudinal nail relative to the leg such that a pointed end of the nail is adjacent to the start point on the buttock;

orienting the nail relative to the leg such that the longitudinal axis of the nail coincides with the reference axis;

inserting the nail through the tissue of the leg such that the longitudinal axis of the nail coincides with the reference axis, said inserting step being initiated by puncturing the outer surface of the leg at the start point with the pointed end of the nail;

inserting the nail further through the tissue such that the longitudinal axis of the nail continues to coincide with the reference axis, and such that the pointed end of the nail punctures the proximal end of the femoral canal; and inserting the nail further into the femoral canal such that the longitudinal axis of the nail continues to coincide with the reference axis.

3. A sterile surgical drape comprising:
a radio-lucent sheet, wherein the sheet comprises a central cutout and a slit extending outward from the central cutout;
adhesive on a major surface of the radio-lucent sheet;
a radio-opaque pattern on the sterile surgical drape, wherein the radio-opaque pattern comprises a perimeter, an interior within the perimeter, and a plurality of intersections distributed within the interior of the radio-opaque pattern; and
a plurality of unique radio-opaque labels on the sterile surgical drape, wherein each radio-opaque label of the plurality of unique radio-opaque labels is located at one intersection of the plurality of intersections in the radio-opaque pattern, and wherein a plurality of uniquely labeled intersections are provided in the interior of the radio-opaque pattern on the sterile surgical drape.

4. A surgical drape according to claim 3, wherein every intersection of the plurality of intersections comprises one of the radio-opaque labels such that one radio-opaque label of the plurality of unique radio-opaque labels is located at every intersection of the plurality of intersections.

5. A surgical drape according to claim 3, wherein the radio-opaque pattern comprises a first set of lines and a second set of intersecting lines, wherein the first set of lines and the second set of intersecting lines form the plurality of uniquely labeled intersections.

6. A surgical drape according to claim 5, wherein some intersections of the plurality of intersections do not include one of the unique radio-opaque labels.

7. A surgical drape according to claim 5, the second set of intersecting lines is oriented at right angles to the first set of lines.

8. A surgical drape according to claim 5, wherein the lines in the first set of lines are located at regular intervals.

9. A surgical drape according to claim 5, wherein the lines in the first set of lines are straight lines.

10. A surgical drape according to claim 5, wherein the lines in the first set of lines are concentric circles.

11. A surgical drape according to claim 10, wherein lines in the second set of lines are radially oriented with respect to the concentric circles of the first set of lines.

12. A surgical drape according to claim 3, wherein the radio-opaque pattern comprises lines of different shapes.

13. A surgical drape according to claim 3, wherein the radio-opaque pattern comprises a plurality of quadrants defined by four labeled intersections of the plurality of labeled intersections.

14. A surgical drape according to claim 3, wherein the radio-opaque pattern comprises a set of concentric circles centered about the central cutout.

15. A surgical drape according to claim 3, wherein the sheet comprises a cylindrical portion adapted to fit over a finger.

16. A surgical drape according to claim 15, wherein the sheet further comprises a hemispherical end portion located at one end of the cylindrical portion.

17. A sterile surgical drape comprising:
a radio-lucent sheet, wherein the sheet comprises a central cutout and a slit extending outward from the central cutout;
adhesive on a major surface of the radio-lucent sheet;
a radio-opaque pattern on the sterile surgical drape, wherein the radio-opaque pattern comprises a first set of lines and a second set of intersecting lines, wherein the first set of lines and the second set of intersecting lines form a plurality of intersections; and
a plurality of radio-opaque labels on the sterile surgical drape, wherein each radio-opaque label of the plurality of radio-opaque labels is located at one intersection of the plurality of intersections in the radio-opaque pattern to provide a plurality of labeled intersections on the sterile surgical drape;
wherein every intersection of the plurality of intersections comprises one of the radio-opaque labels such that every intersection of the plurality of intersections comprises one of the labeled intersections of the plurality of labeled intersections; and
wherein the radio-opaque label at each labeled intersection of the plurality of labeled intersections is unique.

18. A surgical drape according to claim 17, wherein the radio-opaque pattern comprises a plurality of quadrants defined by four labeled intersections of the plurality of labeled intersections.

19. A surgical drape according to claim 17, wherein the radio-opaque pattern comprises a set of concentric circles centered about the central cutout.

20. A surgical drape according to claim 17, wherein the sheet comprises a cylindrical portion adapted to fit over a finger or other appendage.

21. A surgical drape according to claim 20, wherein the sheet further comprises a hemispherical end portion located at one end of the cylindrical portion.

22. A sterile surgical drape comprising:
a radio-lucent sheet comprising a central cutout and a slit extending outward from the central cutout;
adhesive on a major surface of the radio-lucent sheet;
a radio-opaque pattern on the sterile surgical drape, wherein the radio-opaque pattern comprises a plurality of intersections, wherein the radio-opaque pattern comprises a first set of lines and a second set of intersecting lines, wherein the first set of lines and the second set of intersecting lines form a plurality of intersections and further wherein the lines in the first set of lines are concentric circles and the lines in the second set of lines are radially oriented with respect to the concentric circles of the first set of lines; and
a plurality of radio-opaque labels on the sterile surgical drape, wherein each radio-opaque label of the plurality of radio-opaque labels is located at one intersection of the plurality of intersections in the radio-opaque pattern to provide a plurality of labeled intersections on the sterile surgical drape.

23. A surgical drape according to claim 22, wherein the radio-opaque label at each labeled intersection of the plurality of labeled intersections is unique.

24. A surgical drape according to claim 22, wherein every intersection of the plurality of intersections comprises one of the radio-opaque labels such that every intersection of the plurality of intersections comprises one of the labeled intersections of the plurality of labeled intersections.

25. A surgical drape according to claim 24, wherein the radio-opaque label at each labeled intersection of the plurality of labeled intersections is unique.

26. A surgical drape according to claim 22, wherein some intersections of the plurality of intersections do not include one of the radio-opaque labels.

27. A method of medical imaging comprising:
adhering a sterile surgical drape to a patient, wherein the sterile surgical drape comprises:
a radio-lucent sheet comprising a central cutout and a slit extending outward from the central cutout;
a radio-opaque pattern on the sterile surgical drape, wherein the radio-opaque pattern comprises a first set of lines and a second set of intersecting lines, wherein the first set of lines and the second set of intersecting lines form a plurality of intersections and further wherein the lines in the first set of lines are concentric circles and the lines in the second set of lines are radially oriented with respect to the concentric circles of the first set of lines; and
a plurality of radio-opaque labels on the sterile surgical drape, wherein each radio-opaque label of the plurality of radio-opaque labels is located at one intersection of the plurality of intersections in the radio-opaque pattern to provide a plurality of labeled intersections on the sterile surgical drape; and
directing imaging radiation at the patient and through the sterile surgical drape, wherein an image is obtained that includes a pattern image corresponding to the radio-opaque pattern on the surgical drape, the pattern image comprising a plurality of label images corresponding to the radio-opaque labels on the sterile surgical drape.

28. A method according to claim 27, wherein adhering the surgical drape comprises locating the surgical drape on a breast of the patient, wherein the central cutout is located over a nipple on the breast.

29. A method of medical imaging comprising:
applying a sterile surgical drape to a patient by unrolling a cylindrical portion of the sterile surgical drape onto an extremity, finger or other appendage of the patient, wherein the surgical drape comprises:
a radio-lucent sheet forming the cylindrical portion of the surgical drape; and
a radio-opaque pattern on the sterile surgical drape, wherein the radio-opaque pattern comprises a plurality of intersections, and a plurality of radio-opaque labels on the sterile surgical drape, wherein each radio-opaque label of the plurality of radio-opaque labels is located at one intersection of the plurality of intersections in the radio-opaque pattern to provide a plurality of labeled intersections on the sterile surgical drape;
directing imaging radiation at the patient and through the sterile surgical drape, wherein an image is obtained that includes a pattern image corresponding to the radio-opaque pattern on the sterile surgical drape, the pattern image comprising a plurality of label images corresponding to the radio-opaque labels on the sterile surgical drape.

30. A method according to claim 29, wherein applying the surgical drape comprises stretching the radio-opaque sheet.

31. A method according to claim 29, wherein the surgical drape further comprises adhesive on an inner surface of the cylindrical portion, wherein applying the surgical drape comprises adhering the surgical drape to the patient.

* * * * *